(12) United States Patent
Zapol et al.

(10) Patent No.: US 11,826,580 B2
(45) Date of Patent: Nov. 28, 2023

(54) SYSTEM AND METHOD FOR PHOTOTHERAPY FOR PREVENTING OR TREATING CARBON MONOXIDE POISONING

(71) Applicant: The General Hospital Corporation, Boston, MA (US)

(72) Inventors: Warren M. Zapol, Boston, MA (US); R. Rox Anderson, Boston, MA (US); Luca Zazzeron, Boston, MA (US); Walfre Franco, Boston, MA (US); William A. Farinelli, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 235 days.

(21) Appl. No.: 17/202,878

(22) Filed: Mar. 16, 2021

(65) Prior Publication Data

US 2021/0220666 A1 Jul. 22, 2021

Related U.S. Application Data

(62) Division of application No. 15/575,000, filed as application No. PCT/US2016/032845 on May 17, 2016, now Pat. No. 10,953,236.

(Continued)

(51) Int. Cl.
*A61N 5/06* (2006.01)
*A61M 11/00* (2006.01)

(Continued)

(52) U.S. Cl.
CPC .......... *A61N 5/0603* (2013.01); *A61B 1/2676* (2013.01); *A61M 11/00* (2013.01);
(Continued)

(58) Field of Classification Search
CPC ...... A61N 5/0603; A61N 5/062; A61N 5/067; A61N 2005/0604; A61N 2005/0609;
(Continued)

(56) References Cited

U.S. PATENT DOCUMENTS 5,445,608 A * 8/1995 Chen .................... A61N 5/0601
604/20
5,866,015 A 2/1999 Kramer
(Continued)

FOREIGN PATENT DOCUMENTS

CN 2161310 Y 4/1994
JP 2008148951 A 7/2008
(Continued)

OTHER PUBLICATIONS

International Search Report and Written Opinion for International Application No. PCT/US2016/032845 dated Oct. 5, 2016.

*Primary Examiner* — Gary Jackson
*Assistant Examiner* — Sebastian X Lukjan
(74) *Attorney, Agent, or Firm* — QUARLES & BRADY LLP

(57) ABSTRACT

Systems and methods are provided for treating or preventing carbon monoxide poisoning. In particular, systems and methods are provided for a phototherapy treatment or prevention system that delivers light radiation to a patient's body to photodissociate carbon monoxide from hemoglobin.

11 Claims, 31 Drawing Sheets

Related U.S. Application Data

(60) Provisional application No. 62/163,277, filed on May 18, 2015.

(51) Int. Cl.
*A61B 1/267* (2006.01)
*A61M 15/00* (2006.01)
*A61N 5/067* (2006.01)

(52) U.S. Cl.
CPC ............ *A61M 15/009* (2013.01); *A61N 5/062* (2013.01); *A61M 2202/0233* (2013.01); *A61N 5/067* (2021.08); *A61N 2005/063* (2013.01); *A61N 2005/0604* (2013.01); *A61N 2005/0609* (2013.01); *A61N 2005/0651* (2013.01); *A61N 2005/0652* (2013.01); *A61N 2005/0655* (2013.01); *A61N 2005/0662* (2013.01); *A61N 2005/0663* (2013.01)

(58) Field of Classification Search
CPC ...... A61N 2005/063; A61N 2005/0651; A61N 2005/0652; A61N 2005/0662; A61N 2005/0655; A61N 2005/0663; A61B 1/2676; A61M 11/00; A61M 15/009; A61M 2202/0233

See application file for complete search history.

(56) References Cited

U.S. PATENT DOCUMENTS

| | | | |
|---|---|---|---|
| 5,997,842 A * | 12/1999 | Chen | A61N 5/0601 424/9.1 |
| 8,262,868 B2 | 9/2012 | Brooks et al. | |
| 2002/0127224 A1 | 9/2002 | Chen | |
| 2004/0073278 A1 | 4/2004 | Pachys | |
| 2005/0028811 A1* | 2/2005 | Nelson | A61M 16/107 128/200.11 |
| 2007/0118184 A1 | 5/2007 | Danek | |
| 2008/0269849 A1 | 10/2008 | Lewis | |
| 2009/0125088 A1 | 5/2009 | Schleicher et al. | |
| 2009/0259167 A1 | 10/2009 | Sakamoto et al. | |
| 2011/0190749 A1 | 8/2011 | McMillan et al. | |
| 2012/0157905 A1 | 6/2012 | Sehgal | |
| 2013/0101464 A1 | 4/2013 | Smyczynski | |
| 2015/0157714 A1* | 6/2015 | Bornstein | A61N 5/062 604/20 |
| 2016/0271417 A1 | 9/2016 | Kashimura et al. | |
| 2017/0225011 A1 | 8/2017 | Frost | |

FOREIGN PATENT DOCUMENTS

| | | |
|---|---|---|
| JP | 2009000545 A | 1/2009 |
| WO | 2011110277 A1 | 9/2011 |
| WO | 2014004762 A1 | 1/2014 |
| WO | 2014076250 A1 | 5/2014 |
| WO | 2017070155 A1 | 4/2017 |

* cited by examiner

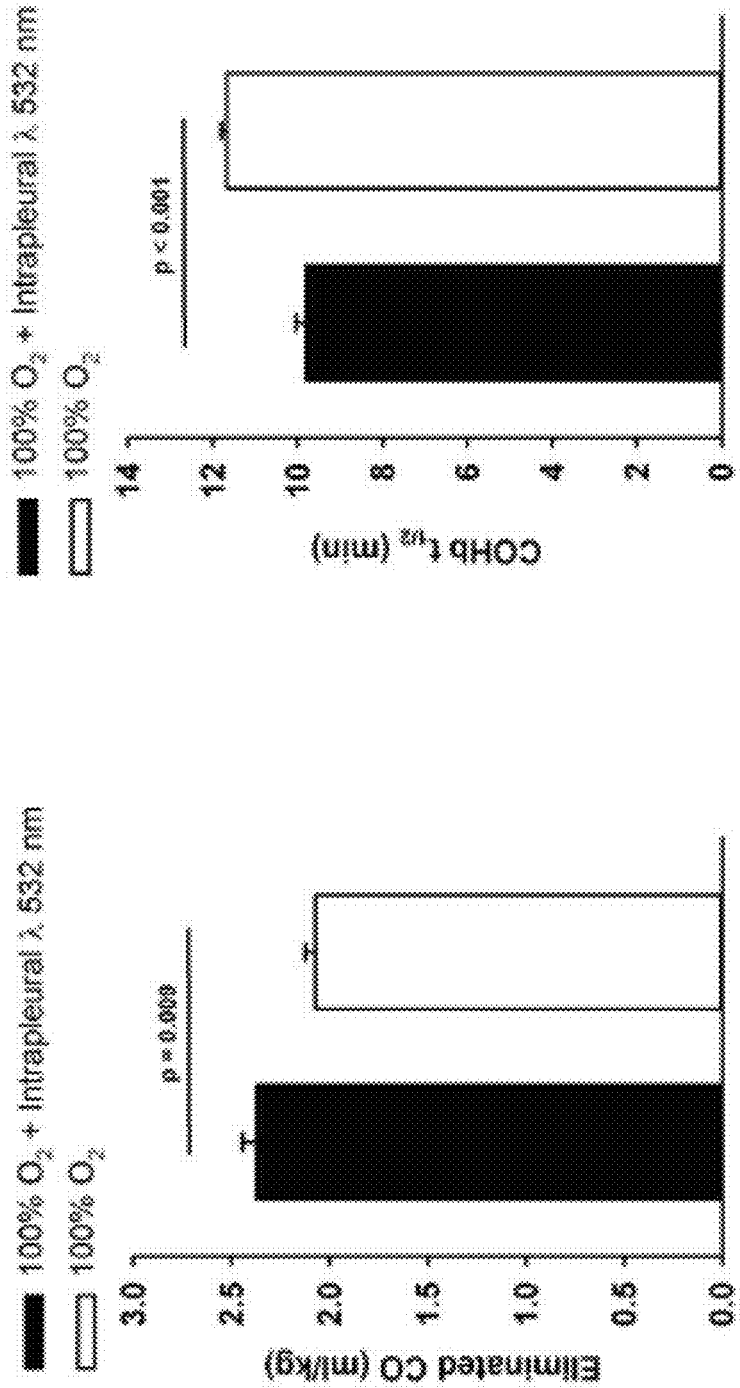

SYSTEM AND METHOD FOR PHOTOTHERAPY FOR PREVENTING OR TREATING CARBON MONOXIDE POISONING

CROSS-REFERENCES TO RELATED APPLICATIONS

This patent application is a division of U.S. patent application Ser. No. 15/575,000, filed on Nov. 17, 2017, which is a United States National Phase entry of PCT Application No. PCT/US2016/032845, filed on May 17, 2016, which is based on and claims priority to U.S. Provisional Patent Application No. 62/163,277, filed May 18, 2015, which are all incorporated by reference in their entirety.

STATEMENT REGARDING FEDERALLY SPONSORED RESEARCH

Not Applicable.

BACKGROUND

Carbon monoxide (CO) poisoning impairs tissue oxygenation as CO avidly binds to hemoglobin (Hb) to form carboxyhemoglobin (COHb), which cannot transport oxygen. Currently, treatment of CO poisoning involves breathing 100% oxygen to attempt to rapidly remove CO. Hyperbaric oxygen therapy and/or hyperventilation therapy or exercise can further increase the rate of CO elimination but the necessary facilities and equipment may be not be readily available. Visible light is also known to photodissociate CO from Hb, with a single photon dissociating one CO molecule from Hb.

Smyczynski suggested in Unites States Patent Application Publication No. 2013/0101464 that light radiation at 540 nanometers (nm) and/or 570 nm could be used to treat CO poisoning by photodissociating COHb in blood passing through an extracorporeal gas exchanger. The treatment system of Smyczynski involves removing and recirculating anticoagulated blood from a patient through an extracorporeal oxygenator. The blood passing through the extracorporeal oxygenator is irradiated with light at either 540 nm and/or 570 nm. The extracorporeal oxygenator is designed such that the blood-light contact surface is as large as possible because the 540 nm and/or 570 nm light does not penetrate deeply into the blood stream before becoming completely absorbed.

The 540 nm and 570 nm light wavelengths are chosen by Smyczynski because these wavelengths align with peaks in the COHb absorption spectra. However, light at 540 nm and 570 nm are poorly transmitted through human tissue, which requires the treatment system of Smyczynski to remove the blood from the patient's body to perform the phototherapy.

BRIEF SUMMARY

The present disclosure provides systems and methods for treating or preventing carbon monoxide poisoning. In particular, systems and methods are provided for a phototherapy treatment or prevention system that delivers light radiation to a patient's body to photodissociate carbon monoxide from hemoglobin. The CO that is removed from the blood is delivered to the alveoli of the lung or the air or other gases surrounding the skin for removal from the body.

In one aspect, the present disclosure provides a phototherapy system for treating or controlling an amount of carbon monoxide poisoning in a patient including a light source configured to output light. The light output from the light source having properties to enable photodissociation of carboxyhemoglobin in the patient. The phototherapy system further including an optical cable coupled to the light source and having one or more waveguides arranged within the optical cable. The one or more waveguides are configured to emit light from the light source directly on a portion of the patient's body to photodissociate carboxyhemoglobin.

In another aspect, the present disclosure provides a phototherapy system for treating or controlling an amount of carbon monoxide poisoning in a patient including a tube having a central lumen, a bag attached to a distal end of the tube, and a light source configured to be fluidly communicated into the bag via the central lumen to emit light into the bag. The light emitted by the light source having properties to enable photodissociation of carboxyhemoglobin in the patient. The tube and bag are configured to be inserted into or placed onto a portion of the patient's body to deliver the light emitted through the bag onto the portion of the patient's body to photodissociate carboxyhemoglobin.

In yet another aspect, the present disclosure provides a phototherapy system for treating or controlling an amount of carbon monoxide poisoning in a patient including a light source in communication with an aerosolizing element, and a tube configured to provide communication between the light source and an airway. The airway configured to provide communication to at least one of a nose and a mouth of the patient. The aerosolizing element is configured to aerosolize the light source to deliver the light source to the patient by ventilation of gas through the airway.

In still another aspect, the present disclosure provides a method for treating or preventing carbon monoxide poisoning in a patient including providing a light source, positioning the light source adjacent to or within a portion of the patient's body, and emitting light from the light source directly onto the portions of the patient's body.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings which may not be drawn to scale.

FIG. 19 shows a phototherapy system in accordance with yet another embodiment of the present disclosure.

FIG. 20 outlines the steps for operating the phototherapy system of FIG. 19 in accordance with one embodiment of the present disclosure.

FIG. 34A shows eliminated carbon monoxide with and without intrapleural phototherapy at 532 nm of rats breathing 100% oxygen after poisoning with 500 ppm CO for 90 minutes.

FIG. 34B shows carboxyhemoglobin half-life with and without intrapleural phototherapy at 532 nm of rats breathing 100% oxygen after poisoning with 500 ppm CO for 90 minutes.

DETAILED DESCRIPTION

Figure 1:
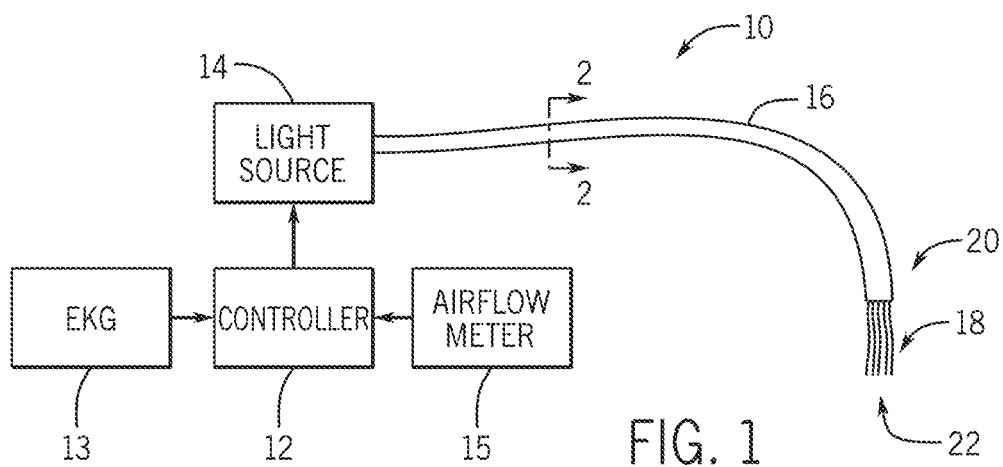
FIG. 1 shows a phototherapy system in accordance with one embodiment of the present disclosure.

The term "visible light" as used herein refers to a portion of the electromagnetic spectrum, generally bound between wavelengths of approximately 380 nanometers (nm) and approximately 750 nm, that is visible to the human eye. One of skill in the art would recognize that the wavelength range of visible light will vary from person to person depending on one's vision. Thus, the range from 380 nm to 750 nm is a generally accepted range and is not meant to be definitively limiting in any way.

Carbon monoxide (CO) poisoning is one of the most common causes of poison-related death worldwide. In the United States, CO inhalation causes approximately 50,000 emergency room visits and more than 400 accidental deaths each year. Even when it is not lethal, CO intoxication is associated with significant morbidity, including memory, attention, and affect disorders.

CO and oxygen have an equal probability of binding to hemoglobin (Hb); however, once bonded, CO binds to Hb with an affinity approximately 200 times greater than oxygen. Therefore, it takes much longer to dissociate CO from Hb decreasing the likelihood of oxygen bonding to Hb.

As described above, phototherapy with visible light can be used to photodissociate COHb. Typically, phototherapy techniques have utilized light wavelengths which are highly absorbed by COHb (e.g., 540 nm and 570 nm). However, the probability of photodissociating COHb during phototherapy can be independent of the wavelength of light. That is, a quantum yield defined as a ratio between a chemical yield (how many molecules are photodissociated from Hb) and how many photons are absorbed can be independent of the wavelength of light. The CO poisoning treatment or prevention systems and methods of the present disclosure leverage this non-intuitive phenomenon by utilizing wavelengths of light that are poorly absorbed by COHb but can sufficiently penetrate human tissue. In one non-limiting example, these wavelengths of light may be between 590 nm and 630 nm.

Utilizing wavelengths of light that can sufficiently penetrate human tissue enable the CO poisoning treatment or prevention systems and methods of the present disclosure, described in great detail below, to provide phototherapy directly to one or more portions of a patient's body that offer access to a large volume of blood flow. One portion of the patient's body of particular interest is the lungs and, in particular, the pulmonary vasculature. Visible light radiated within the patient's body could reach the pulmonary vasculature if the radiated visible light could sufficiently penetrate the interfering tissue. The pulmonary vasculature, including arteries, alveolar-capillary networks, and veins, provides access to a large volume of blood flow (the entire cardiac output) that is constantly re-circulating during every breathing cycle due to ventilation-perfusion matching. In a healthy human, the entire blood volume of approximately 5 liters circulates through the lung once each minute. Additionally, the pulmonary vasculature is surrounded by the alveoli where photodissociated CO can be released into the alveolar gas space and expelled from the patient's body upon exhalation.

Phototherapy with visible light also has the potential to photodissociate oxyhemoglobin ($HbO_2$) in the lung, which could hinder the treatment or prevention of CO poisoning by further impairing tissue oxygenation. However, the quantum yield associated with the photodissociation of $HbO_2$ using visible light is approximately 0.008, while the quantum yield associated with the photodissociation of COHb using visible light is approximately 0.5 or higher. Thus, a significantly larger portion of the COHb is photodissociated to deoxyHb as compared to the $HbO_2$ which aids in the restoration of $HbO_2$ levels in the blood.

The following detailed description is directed towards various non-limiting examples of systems and methods that can provide phototherapy to treat or prevent CO poisoning by radiating visible light into the pulmonary vasculature or skin.

FIG. 1 illustrates one non-limiting example of a phototherapy system 10 for treating or preventing CO poisoning. The phototherapy system 10 includes a controller 12 in communication with a light source 14. The light source 14 can be in the form of a laser configured to output visible light at a wavelength between approximately 590 nm and 650 nm. In other non-limiting examples, the light source 14 may be in the form of a light-emitting-diode (LED), or any other visible light emitting device known in the art. The controller 12 is configured to control the pulse width, frequency, and energy output of the light source 14. The controller 12 is also configured to cycle the light source 14 on and off, and control the duration the light source 14 is turn on, as desired. Additionally, as shown in FIG. 1, the controller 12 is in communication with an EKG signal 13 of a patient and an airflow meter 15. The airflow meter 15 is configured to measure the flow rate of oxygen or air through the patient's trachea and bronchial tree and enables the controller 12 to identify when the patient is inhaling and exhaling. Thus, the controller 12 may be configured to gate an optical signal supplied to the light source 14 to end inspiration thereby saving power and reducing heating of lung tissue, and allowing immediate-subsequent exhalation of CO rich gas. Additionally or alternatively, the controller 12 can be in communication with a measurement device, for example a transcutaneous COHb pulse oximeter, capable of continuously measuring the arterial CO concentration in a patient's blood. The controller 12 can be configured to turn off the light source 14 once the CO concentration in the patient's blood has sufficiently reduced.

As described above, peak absorption of visible light by COHb occurs near 540 nm and 570 nm. The absorption of visible light by COHb substantially decreases as wavelength increases above 570 nm, with little to no absorption occurring above 690 nm. Although the absorption of visible light by COHb substantially decreases above 570 nm, the penetration depth of visible light into, or through, human tissue increases as wavelength increases above approximately 570 nm. Thus, the wavelength of light output by the light source 14 is capable of sufficiently penetrating into, or through, human tissue and also capable of being absorbed by COHb.

In other non-limiting examples, the light source 14 may be configured to output light at a wavelength between approximately 380 nm and approximately 750 nm. In still other non-limiting examples, the light source 14 may be configured to output light at any wavelength absorbed by COHb, as desired.

Figure 2:
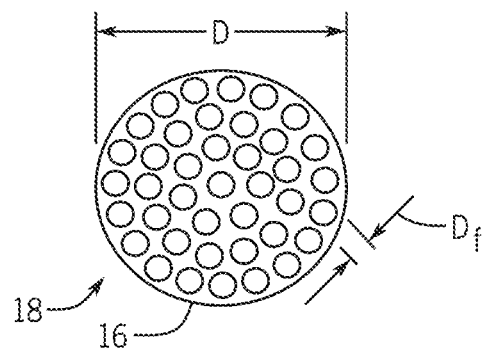
FIG. 2 shown is a cross-sectional view of an optical cable of the phototherapy system of FIG. 1 taken along line 2-2.

With reference to FIGS. 1 and 2, the light source 14 is coupled to an optical cable 16 such that the light output from the light source 14 is transmitted through one or more waveguides 18 arranged within and along the optical cable 16. The optical cable 16 defines a substantially cylindrical shape and is dimensioned such that a diameter D of the optical cable 16 is small enough to ensure a patient can be ventilated or breathe around the optical cable 16 if inserted into the patient's esophagus or trachea. In one non-limiting example, the diameter D of the optical cable 16 can be less than approximately ten millimeters (mm). In other non-limiting examples, the optical cable 16 may define a different shape, as desired.

The optical cable 16 may be fabricated from a flexible, biocompatible material capable of bending without deforming while being inserted into the patient's esophagus or respiratory tract. Alternatively or additionally, the optical cable 16 can be received within a flexible, biocompatible tube, such as a PVC tube, a PTFE tube, a PES tube, or any flexible, biocompatible tube known in the art. The optical cable 16 or tube can be part of an endotracheal tube, or an endotracheal tube fitted with an extra lumen (or double lumen endotracheal tube such as used to obtain lung isolation in thoracic surgery). The waveguides 18 can be placed separately in each main stem bronchus, or passed beyond, under direct visualization with a fiber optic bronchoscope.

The waveguides 18 are fabricated from a flexible, biocompatible material that is capable of efficiently transmitting the light output by the light source 14, such as glass, plastic, liquid, gel, or any other viable material known in the art. In the illustrated non-limiting example, the waveguides 18 are one or more optical fibers. In another non-limiting example, the waveguides 18 can be collagen gel, which, in addition to being flexible and biocompatible, is also biodegradable. The waveguides 18 can each define a waveguide diameter $D_f$ and can be dimensioned to be longer than the optical cable 16 such that a portion of the waveguides 18 protrude from a distal end 20 of the optical cable 16. The waveguide diameter $D_f$ can be between approximately 5 micrometers (μm) and 1000 μm. In other non-limiting examples, the waveguide diameter $D_f$ can be less than 5 μm or greater than 1000 μm, as desired.

In the illustrated non-limiting example of FIG. 1, each of the waveguides 18 protrude an equal distance from distal end 20 of the optical cable 16. In another non-limiting example, the waveguides 18 can each protrude a different distance from the distal end 20 of the optical cable 16. The distance that each waveguide 18 protrudes can be a fixed predetermined value that is different or the same for each waveguide 18 or, in other non-limiting examples, the distance that each waveguide 18 protrudes from the optical cable 16 can be variably controlled by a user of the phototherapy system 10. The distal end 20 of the optical cable 16 may include a stent-like structure (not shown) that contains the portion of the waveguides 18 that protrude from the optical cable 16. The stent-like structure can aid in preventing the waveguides 18 from contacting tissue surfaces when the optical cable 16 is inserted into the esophagus or the respiratory tract of a patient.

As shown in FIG. 2, the optical cable 16 includes 40 waveguides 18. However, the phototherapy system 10 is not limited to this configuration as the number of waveguides 18 can be different in other configurations. For example, the optical cable 16 can include one waveguide 18, or the optical cable 16 can include any number of waveguides 18, as desired, as long as the waveguide diameter $D_f$ is small enough to fit the desired number of waveguides 18 within the diameter D of the optical cable 16.

Figure 3:
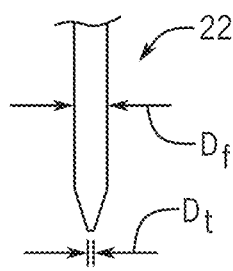
FIG. 3 shows a tip defining a substantially conical shape in accordance with one embodiment of the present disclosure.
Figure 4:
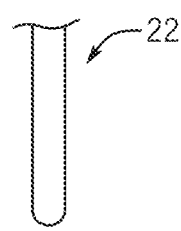
FIG. 4 shows a tip defining a substantially round shape in accordance with another embodiment of the present disclosure.
Figure 5:
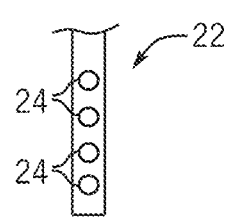
FIG. 5 shows a tip including one or more diffusing elements in accordance with yet another embodiment of the present disclosure.

With reference to FIGS. 1-5, each of the waveguides 18 include a tip 22 arranged distally from the light source 14. The tips 22 are configured to emit the light output from the light source 14 transmitting through the waveguides 18. The tips 22 can be configured to diffusely emit light by shaping the tips 22, as shown in FIGS. 3 and 4, and/or by including diffusion optics or elements on or within to the tips 22, as shown in FIG. 5. Diffusely emitting light from the tips 22 enables the phototherapy system 10 to uniformly treat a large volume of tissue (e.g., gas exchanging lung) within a patient. Additionally, diffusely emitting light from the tips 22 or gating illumination with end-inhalation of fresh gas reduces the irradiance (energy per unit area) subjected to the tissue being treated within a patient, which reduces the probability of the treated tissue overheating.

As shown in FIG. 3, in one non-limiting example, the tips 22 can define a substantially conical shape which tapers from the diameter $D_f$ of the waveguide down to a tip diameter Dc, where $D_t$ is less than $D_f$. The tapering from $D_f$ down to $D_t$ enables the tips 22 to diffusely emit the light from the light source 14 by emitting light radially around and axially along the tips 22. As shown in FIG. 4, in another non-limiting example, the tips 22 can define a substantially round shape. The rounded shape of the tips 22 enables the tips 22 to diffusely emit light radially around the tips 22. The illustrated tips 22 of FIG. 4 defines a tip diameter $D_t$ approximately equal to the diameter of the waveguide $D_f$. Alternatively, the tip diameter $D_t$ may be greater than or less than the diameter of the waveguide $D_f$, as desired. It would be known by one of skill in the art that other shapes, or geometries, of the tips 22 are possible to aid in the diffusion of the light emitted from the tips 22.

As shown in FIG. 5, in yet another non-limiting example, the tips 22 can include one or more diffusing elements 24 arranged on or within the tips 22. The diffusing elements 24 can be in the form of notches machined into the tips 22, optical lenses arranged on or within the tips 22, scattering particles arranged within the tips 22, or any other diffusing element known in the art. Regardless of the form of the diffusing elements 24, once the light output from the light source 14 transmitting through the waveguides 18 contacts the diffusing elements 24, the diffusing elements 24 scatter the incident light, which then causes light to emit diffusely and radially around the sides of the tips 22.

In still other non-limiting examples, the tips 22 may leverage beam divergence and natural scattering through air or water to diffusely propagate the light emitted from the tips 22.

Figure 6:
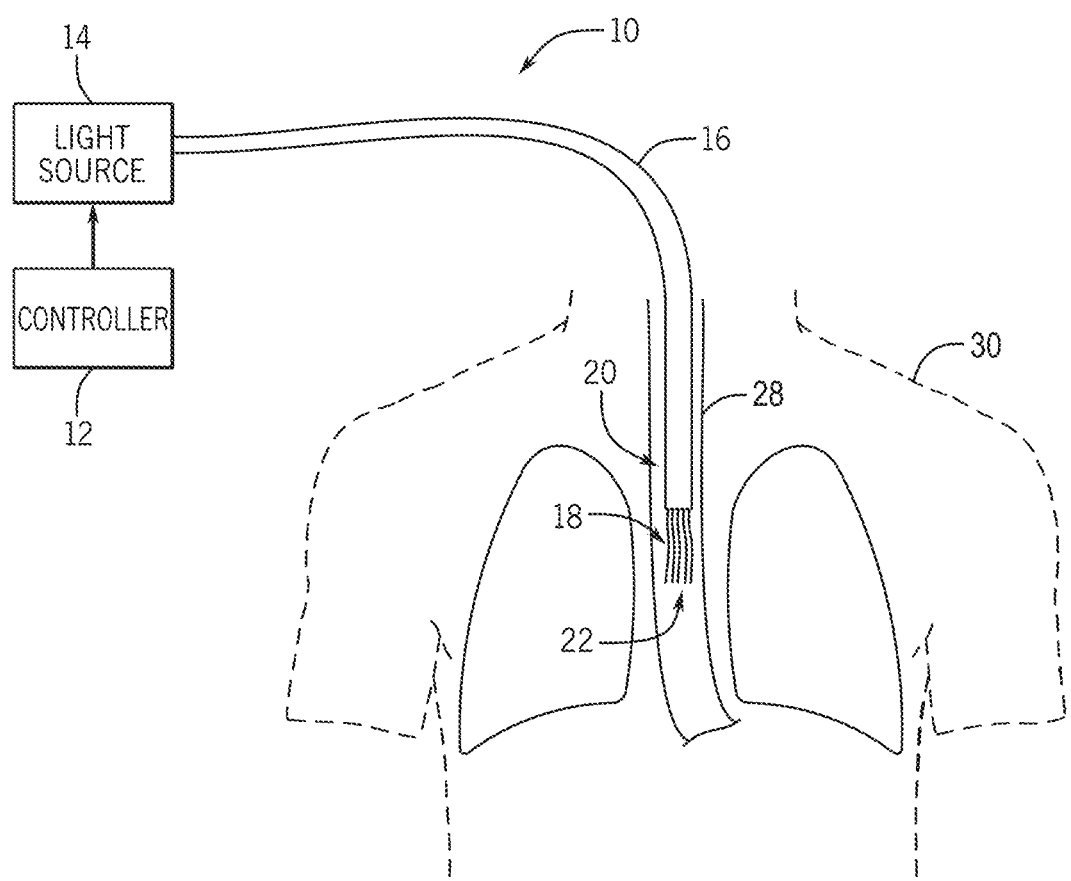
FIG. 6 shows an optical cable of the phototherapy system of FIG. 1 inserted into an esophagus of a patient.

Turning to FIG. 6, the optical cable 16 may be configured to be inserted into an esophagus 28 of a patient 30 to position the waveguides 18 within the esophagus 28. The optical cable 16 can be inserted into the esophagus 28, by a user of the phototherapy system 10, orally or through the nares of the patient 30. The distal end 20 of the optical cable 16, and thereby the tips 22, can be positioned at any desired location along the esophagus 28. In one non-limiting example, the optical cable 16 can include incremented distance markers that provide a user of the phototherapy system 10 an indication of how far the distal end 20 of the optical cable 16 is inserted into the esophagus 28.

Figure 7:
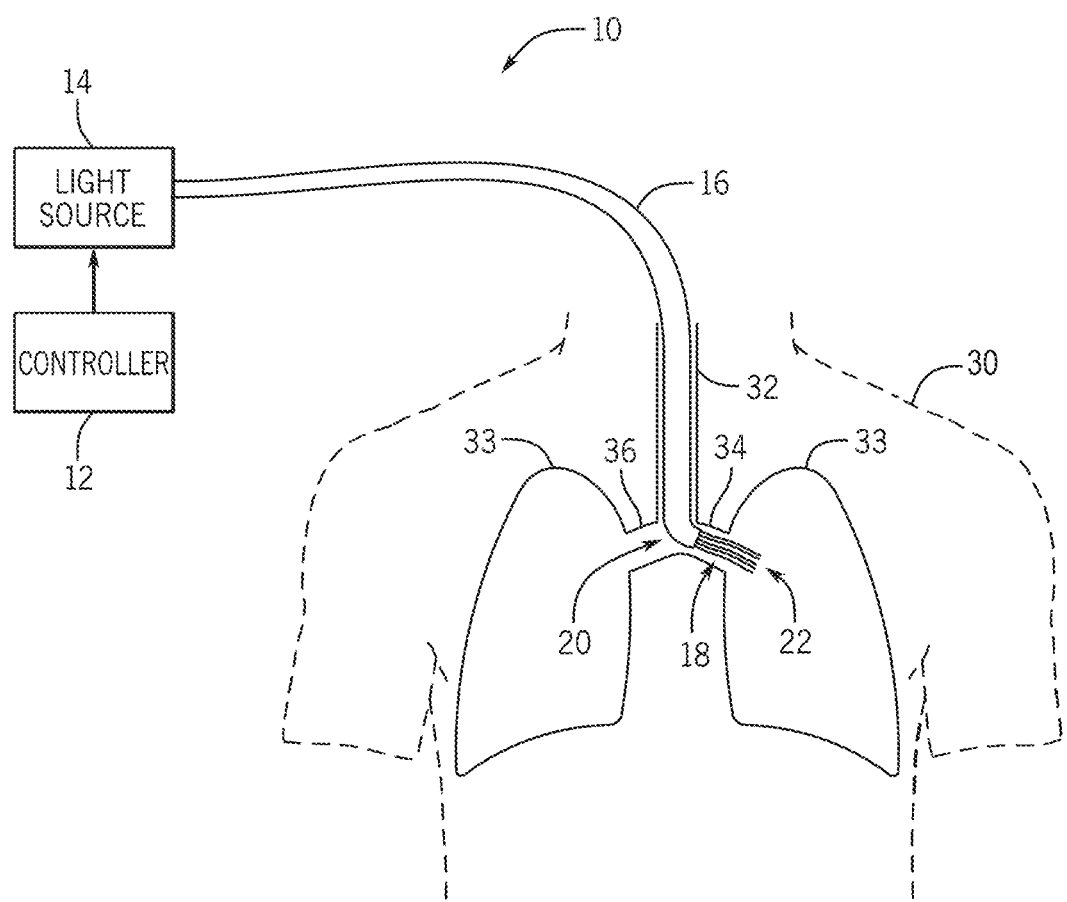
FIG. 7 shows an optical cable of the phototherapy system of FIG. 1 inserted into a right mainstem bronchus of a patient.

Additionally or alternatively, as shown in FIG. 7, the optical cable 16 may be configured to be inserted into a trachea 32 of the patient 30 to position the waveguides 18 within the trachea 32 and/or the bronchial tree of the patient 30. In one non-limiting example, the optical cable 16 can be inserted through or along side an intubation tube. Alternatively or additionally, the optical cable 16 can be inserted orally or through the nares of the patient 30. The optical cable 16 can be manipulated by a user of the phototherapy system 10 to position the distal end 20 of the optical cable 16, and thereby the tips 22, at any desired location along the trachea 32 or the bronchial tree. For example, as shown in FIG. 7, the distal end 20 of the optical cable 16 is located within the left mainstem bronchus 34 of the patient 30. Alternatively, the distal end 20 of the optical cable 16 can be manipulated by a user of the phototherapy system 10 to be located within the right mainstem bronchus 36 of the patient 30. The diameter D of the optical cable 16 can be dimensioned to be sufficiently small such that the optical cable 16 can be inserted past either the right or left mainstem bronchus into smaller airways.

Alternatively or additionally, the optical cable 16 can be configured to be inserted through a chest tube to position the waveguides 18 in the pleural spaces surrounding the lungs 33 of the patient 30, or the optical cable 16 can be configured to position the waveguides 18 at any location on or within a patient's body to provide phototherapy, as desired.

Figure 9:
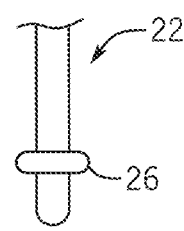
FIG. 9 shows a tip including a fin to control a drag force across the tip in accordance with another embodiment of the present disclosure.
Figure 8:
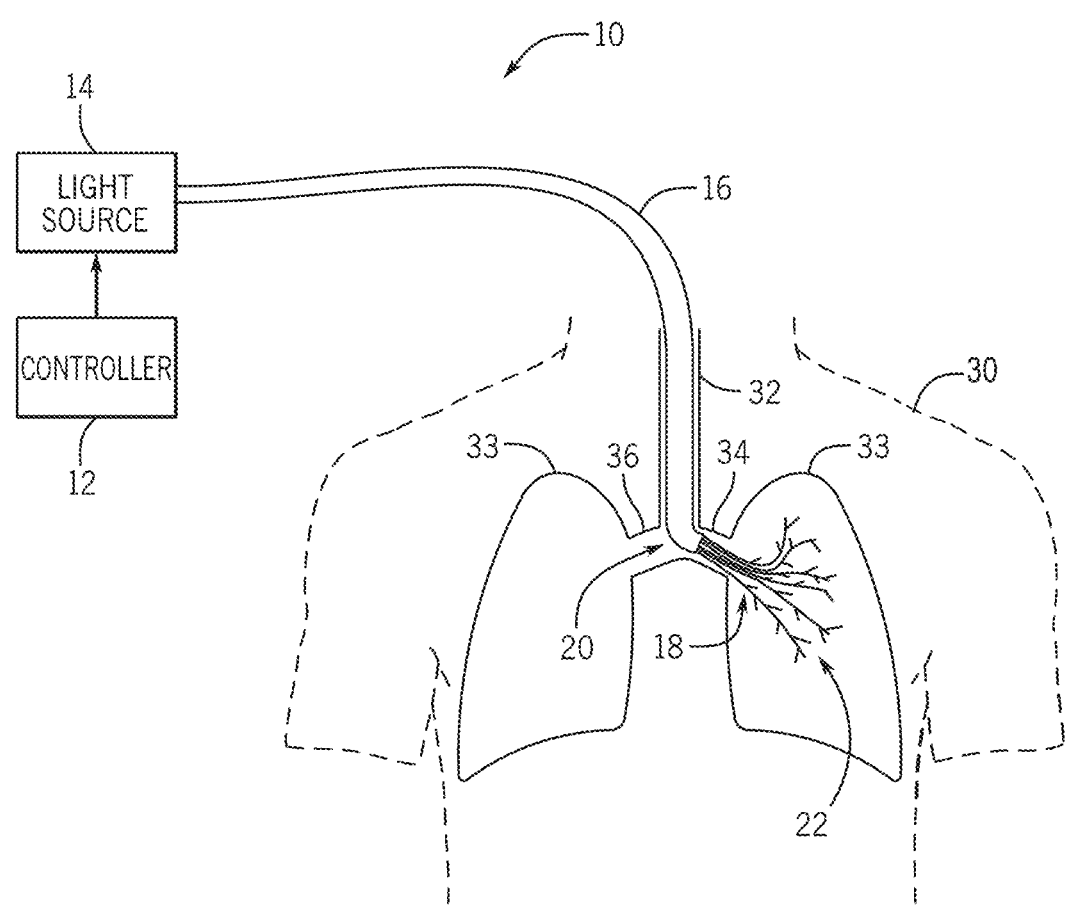
FIG. 8 shows waveguides of the phototherapy system of FIG. 1 displaced throughout the bronchial tree of a patient.

In one non-limiting example, the waveguide diameter $D_f$ of the waveguides 18 can be sufficiently small and the material the waveguides 18 are fabricated from can be sufficiently flexible to enable the waveguides 18 to be positioned by air flowing through the respiratory tract of a patient. That is, when the optical cable 16 is inserted through the trachea of a patient, the waveguides 18 can be carried by the gas flowing through the patient's respiratory tract to position the waveguides 18 throughout the bronchial tree when the patient 30 inhales (or is ventilated with positive pressure), as shown in FIG. 8. To aid in this process, each of the tips 22 may include a fin 26, as shown in FIG. 9. The fins 26 are configured to increase the drag force, or gas resistance, across the tips 22 to aid in displacing the waveguides 18 during a forced mechanical deep inhalation or large spontaneous tidal volume, driven by positive pressure ventilation or a voluntary deep breath. Alternatively, the waveguides 18 can be displaced during a positive pressure deployment applied by a user of the phototherapy system 10. Each of the fins 26 can vary in size, shape, or any other physical characteristic that would influence the drag force, to promote distributing the tips 22 throughout the bronchial tree. Alternatively or additionally, the tips 22 may be coated with an adhesive that adheres to tissue and/or mucus within bronchial tree of the patient 30.

Figure 10:
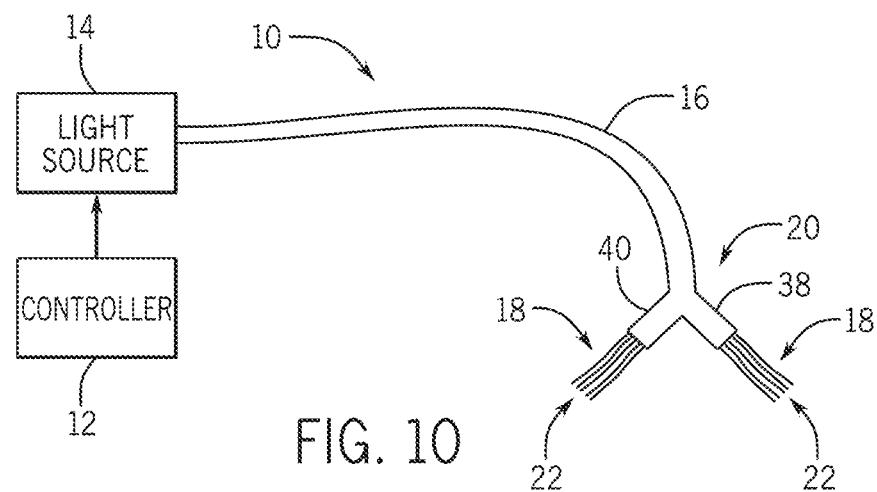
FIG. 10. shows the phototherapy system of FIG. 1 where a distal end of an optical cable is split into a first distal section and a second distal section.
Figure 11:
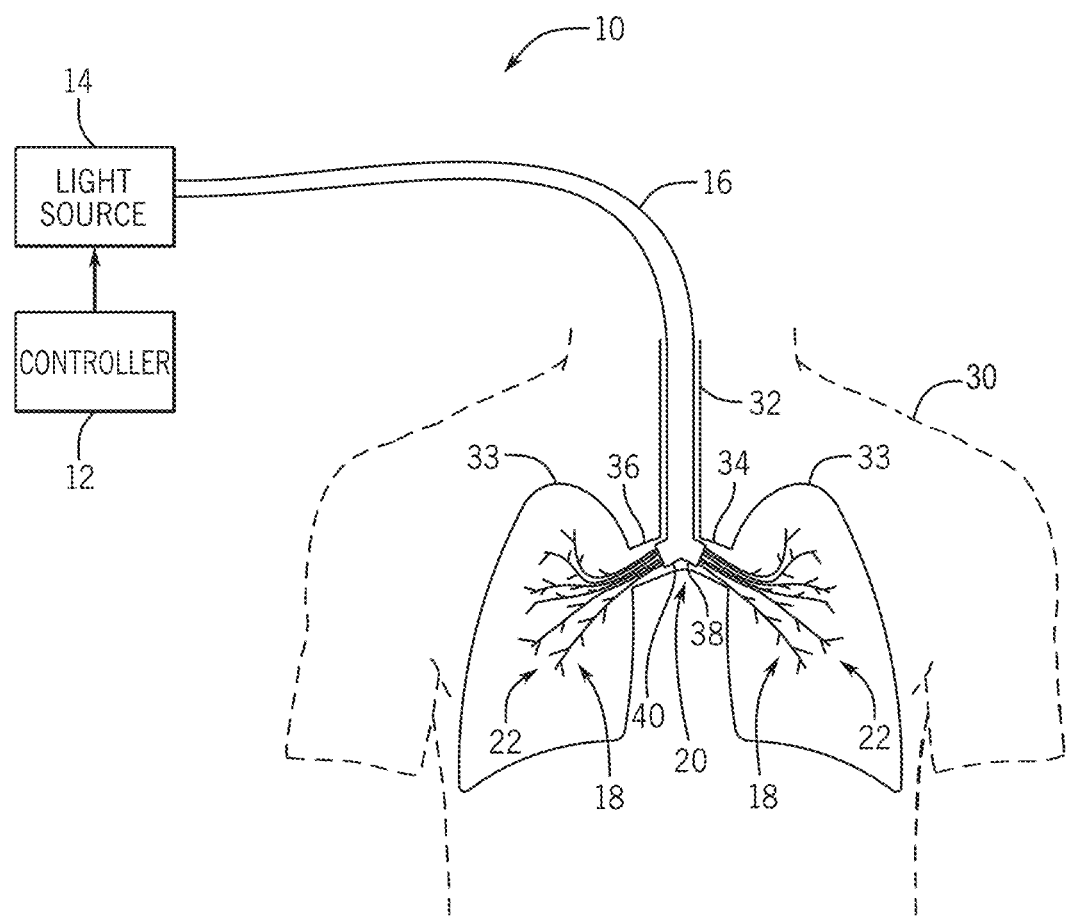
FIG. 11 shows waveguides of the phototherapy system of FIG. 10 displaced throughout the bronchial tree of a patient.

FIG. 10 shows another non-limiting example of the phototherapy system 10 where the distal end 20 of the optical cable 16 is split into a first distal section 38 and a second distal section 40. A fraction of the waveguides 18 protrude from the first distal section 38 and the remaining fraction of the waveguides 18 protrude from the second distal section 40. The first distal section 38 and the second distal section 40 are dimensioned such that either the first distal section 38 or the second distal section 40 can be received within either the left mainstem bronchus 34 or the right mainstem bronchus 36 of the patient 30, when the optical cable 16 is inserted through the patient's trachea 32, as shown in FIG. 11. Additionally, in this non-limiting example, the waveguides 18 can be displaced throughout the bronchial tree, for example with the aid of the fins 26, in both lungs 33 of the patient 30, as shown in FIG. 11.

Figure 12:
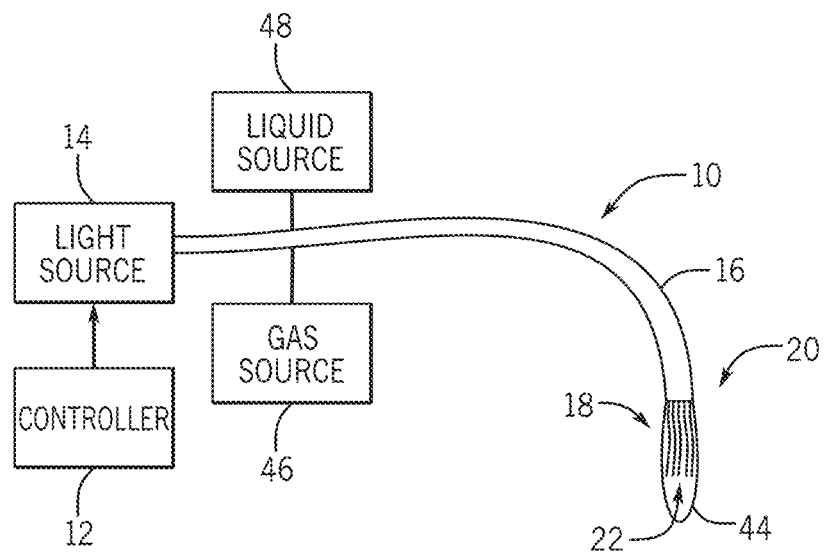
FIG. 12 shows the phototherapy system of FIG. 1 including a balloon, a liquid source, and a gas source.
Figure 13:
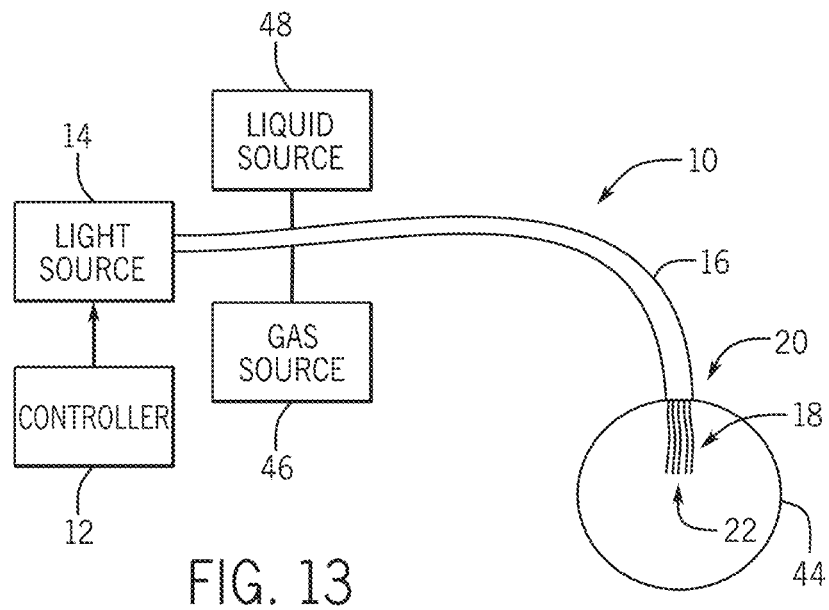
FIG. 13 shows the phototherapy system of FIG. 12 where the balloon is in an inflated state.
Figure 14:
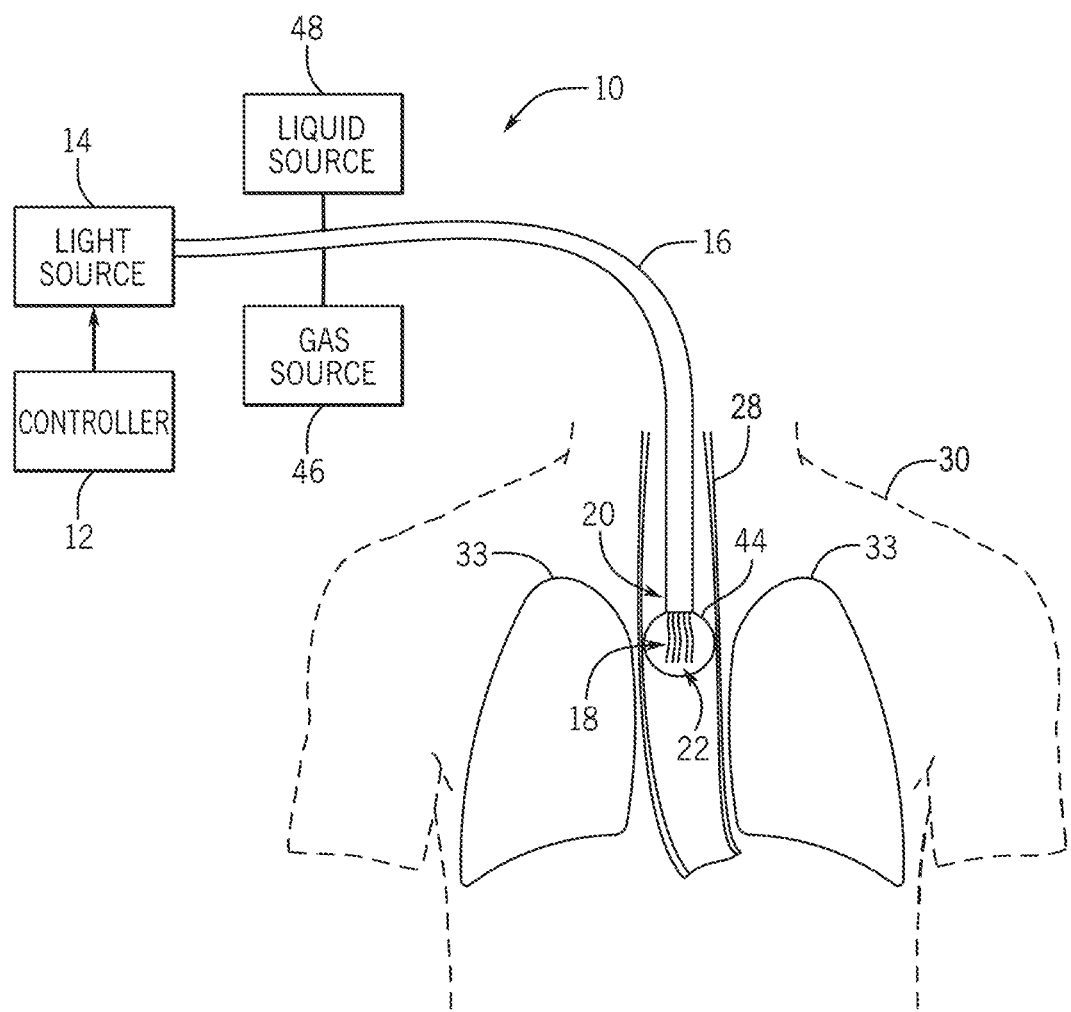
FIG. 14 shows an optical cable of the phototherapy system of FIG. 13 inserted into an esophagus of a patient.

FIGS. 12 and 13 show yet another non-limiting example of the phototherapy system 10 where a balloon 44 may be attached to the distal end 20 of the optical cable 16. The balloon 44 encloses the portions of the waveguides 18 that protrude from the distal end 20 of the optical cable 16. The balloon 44 is fabricated from a biocompatible material that is capable of efficiently transmitting the light emitted from the tips 22. The balloon 44 is in communication with a gas source 46 and/or a liquid source 48 via a fluid passageway arranged within and along the optical cable 16. The balloon 44 is configured to be expandable between a deflated state (FIG. 12) and an inflated state (FIG. 13). Either the gas source 46 and/or the liquid source 48 can be used to expand the balloon 44 between the deflated state (FIG. 12) and the inflated state (FIG. 13). In one non-limiting example, the gas source 46 may be a pressurized supply of air or oxygen. When the optical cable 16 is inserted into the esophagus 28 of the patient 30 and the balloon 44 is in the inflated state, as shown in FIG. 14, the balloon 44 can expand and thin the walls of the esophagus 28 thereby minimizing the thickness of the wall of the esophagus 28. This can minimize the amount of tissue that the light emitted from the tips 22 has to penetrate while applying phototherapy within the esophagus 28 of the patient 30.

The gas source 46 and/or the liquid source 48 can provide a cooling fluid within the balloon 44. The cooling fluid can reduce heating of tissue irradiated by the light emitted from the tips 22 of the waveguides 18. Thus, when the cooling fluid is present within the balloon 44, the tissue receiving phototherapy can tolerate a higher power light output from the light source 14 compared to when no cooling fluid is present within the balloon 44. Additionally or alternatively, the cooling fluid can be a low absorption fluid, such as lipid emulsions used for feeding IV, capable of transmitting and diffusely scattering the light output from the light source 14.

Figure 15:
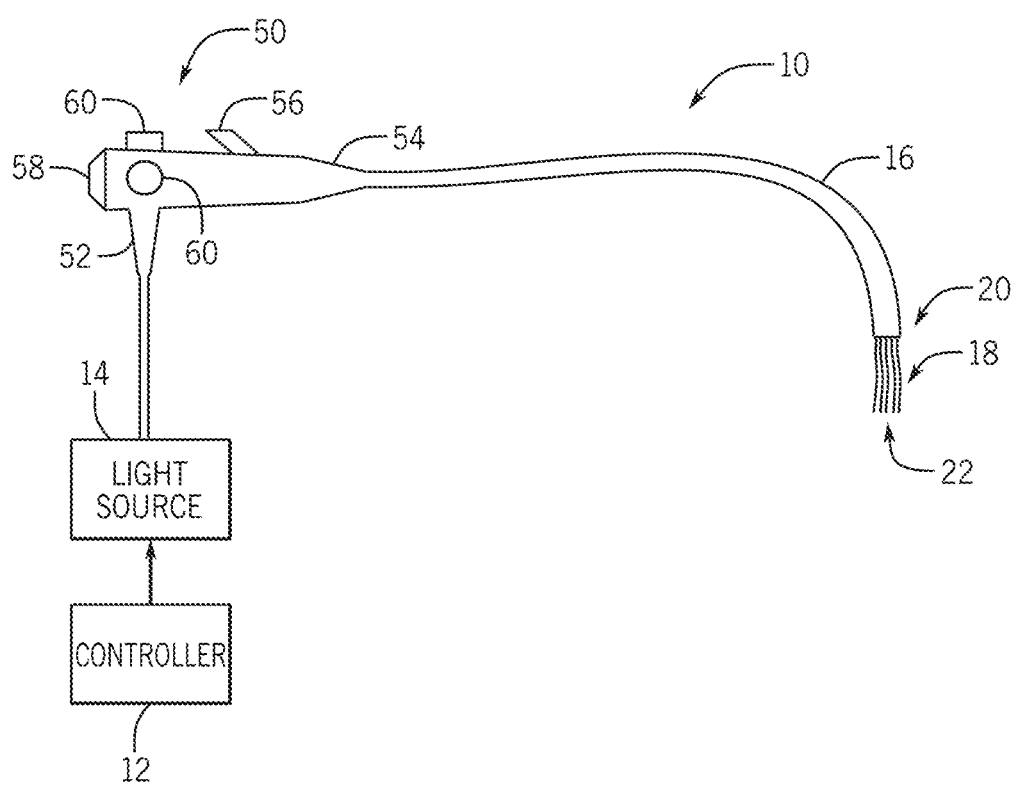
FIG. 15 shows the phototherapy system of FIG. 1 integrated with a bronchoscope in accordance with one embodiment of the present disclosure.

FIG. 15 shows another non-limiting example of the phototherapy system 10 where the phototherapy system 10 is integrated into a bronchoscope 50. The bronchoscope 50 includes an optical port 52 coupled to the light source 14, a work port 54 coupled to the optical cable 16, a suction port 56, a viewing port 58, and one or more adjustment mechanisms 60 that are mechanically coupled to the optical cable 16. The suction port 56 is in communication with a suction passageway that is arranged within and along the optical cable 16. The viewing port 58 enables a user of the phototherapy system 10 to view images acquired by optics arranged on the distal end 20 of the optical cable 16. The adjustment mechanisms 60 are configured to adjust the position of the distal end 20 of the optical cable 16.

The suction port 56 can be connected to a suction device configured to produce a vacuum throughout the suction passageway for removing fluid samples from the trachea and/or bronchial tree of a patient. The viewing port 58 and the adjustment mechanisms 60 enable a user of the phototherapy system 10 to view and adjust the position of the distal end 20 of the optical cable 16 in real time.

Figure 16:
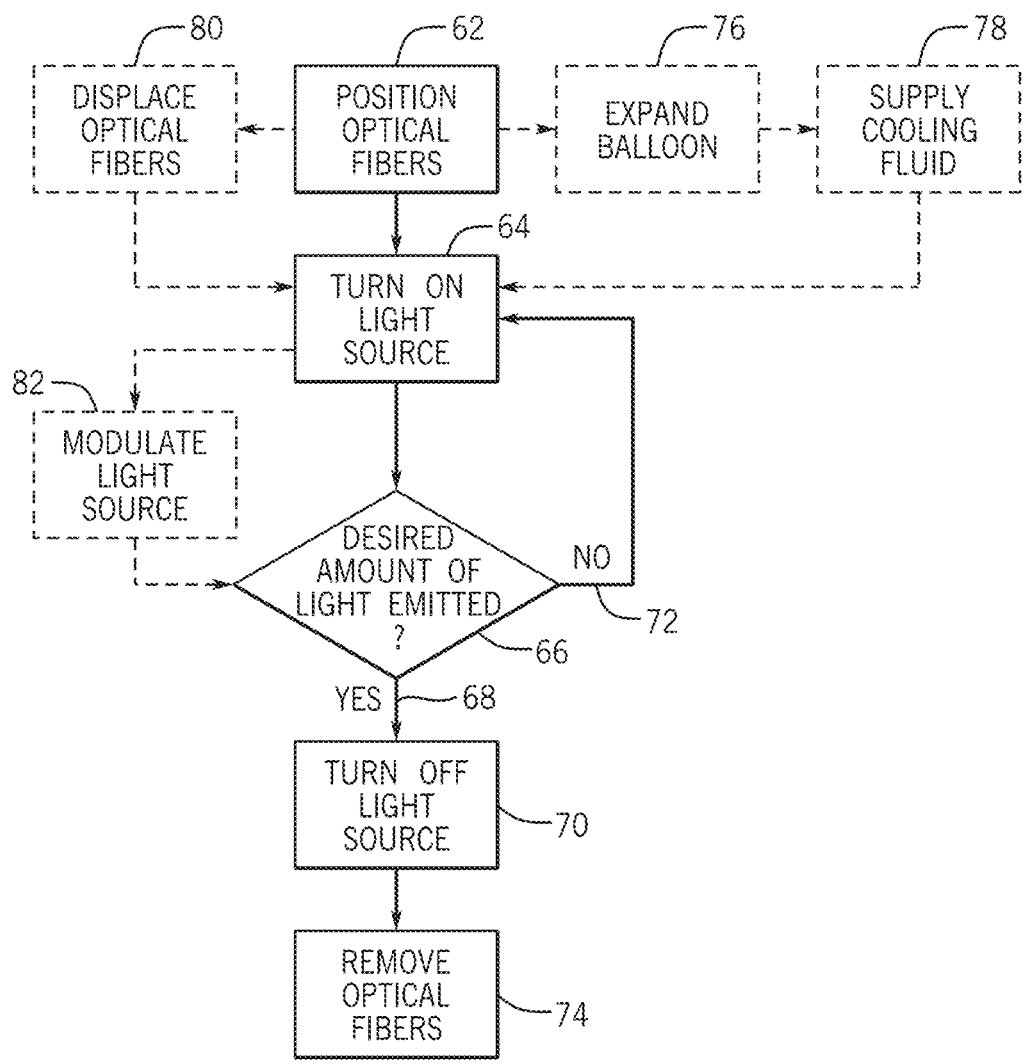
FIG. 16 outlines the steps for operating the phototherapy system of FIG. 1 in accordance with one embodiment of the present disclosure.

One non-limiting example of operation of the phototherapy system 10 will be descried with reference to FIGS. 1-16. In operation, a user of the phototherapy system 10 can treat a patient with CO poisoning. The steps the user can perform to treat the patient with CO poisoning are illustrated in FIG. 16. The user of the phototherapy system 10 is, typically, a trained healthcare professional. It should be known that the following description of the treatment of CO poisoning using the phototherapy system 10 is one exemplary non-limiting example and, as will be recognized by one of skill in the art, alternative methods or different steps may be used.

As shown in FIG. 16, first, the waveguides 18 are positioned at step 62 by the user such that the waveguides 18 directly emit light onto a portion of the patient's body (e.g., lungs or skin). Positioning the waveguides 18 at step 62 can be accomplished by inserting the optical cable 16 into the esophagus, trachea, bronchial tree, or pleural spaces (e.g., via a thoracotomy tube or tubes) of the patient. Alternatively, the waveguides 18 can be positioned on, within, or upon (e.g. skin) any portion of the patient's body, as desired. In another non-limiting example, the waveguides 18 can be positioned at step 62 to directly emit light onto the lungs of the patient following a thoracotomy. In still another non-limiting example, the waveguides 18 can be positioned at step 62 to directly emit light onto all or a portion of the patient's skin. In this non-limiting example, the patient may be provided pure oxygen (i.e., 100% $O_2$) to breathe and/or the body surface (i.e., the skin) of the patient may be flushed with, or exposed to, pure oxygen.

Following the positioning of the waveguides 18 at step 62, the user then turns on the light source 14 via the controller 12 at step 64. Once the light source 14 is turned on at step 64, light is output from the light source 14 through the waveguides 18 and emitted onto the portion of the patient's body. As described above, in one non-limiting example, the light source 14 can be configured to output light at a wavelength between 590 nm and 650 nm, which are wavelengths that are capable of penetrating into, or through, human tissue and being absorbed by COHb. Therefore, whether the waveguides 18 are positioned within the esophagus, trachea, bronchial tree, or pleural spaces of the patient, the light emitted from the waveguides 18 penetrates through the surrounding tissue to reach the pulmonary vasculature of the patient. With the light source turned on at step 64, the light emitted from the light source 14 and through the waveguides 18 reaches the pulmonary vasculature. In the pulmonary vasculature, the emitted light is absorbed by COHb thereby photodissociating the CO from the Hb. Since the alveolar partial pressure of oxygen in the lungs or surrounding the body can be much greater that the partial pressure of CO in the pulmonary vasculature or skin vasculature, the oxygen pressure gradient drives oxygen molecules to bind to deoxygenated Hb at a far greater rate than CO. Thus, the CO is photodissociated from COHb into the alveolus of the patient and exhaled during the next tidal gas exhalation.

Once the light source 14 is turned on at step 64, the controller 12 determines at step 66 if a desired amount of light has been emitted. If so 68, the light source 14 is turned off at step 70 either automatically by the controller 12 or manually by the user via the controller 12. If not 72, the light source 14 continues to be on until the controller 12 determines at step 66 that the desired amount of light has been emitted. The desired amount of light emitted by the light source 14 can be correlated to achieving a balance between providing enough phototherapy to lower the patient's arterial COHb levels (which can be measured non-invasively and continuously using a digital pulse CO-oximeter (Massimo Corp.)), and preventing the surrounding tissue irradiated by the light emitting from the waveguides 18 from overheating. The user can control the pulse width, frequency, and energy output of the light source 14 via the controller 12 such that the power output by the light source 14 does not damage the irradiated tissue but still provides sufficient photodissociation of COHb. Additionally, the user can instruct the controller 12 to turn off the light source 14 after a predetermined amount of time to ensure that the desired amount of light is emitted and the irradiated tissue is not damaged. Alternatively or additionally, the light provided from the light source 14 can be gated via the controller 12 to some portion of the inspiration of fresh gas, and then turned off during exhalation to reduce tissue heating.

Once the controller 12, or the user, has turned off the light source 14 at step 70, the waveguides 18 can be removed at step 74 from the esophagus, trachea, bronchial tree, pleural spaces, or other portion of the patient's body. Alternatively or additionally, the waveguides 18 be left in the patient's body as the waveguides 18 can be fabricated from a biodegradable material, as described above.

Alternatively or additionally, the optical cable 16 can include a balloon 44 attached to the distal end 20 of the optical cable 16, as described above. In this non-limiting configuration, once the user has positioned the waveguides 18 at step 62 in a desired location along the esophagus of the patient, the balloon 44 can be expanded at step 76 to the inflated state thinning the walls of the esophagus. Once the balloon 44 is expanded at step 76, cooling fluid can be supplied at step 78 within the balloon 44 from either the gas source 46 or the liquid source 48 to cool the surrounding tissue. With the cooling fluid supplied at step 78 inside the balloon, the light source 14 can then be turned on at step 64 by the user via the controller 12.

Alternatively or additionally, the tips 22 of the waveguides 18 can include fins 26, as described above. In this non-limiting configuration, once the user has positioned the waveguides 18 at step 62 in a desired location within the distal trachea or bronchial tree of the patient, the waveguides 18 can be displaced at step 80 during inhalation or a positive pressure deployment to distribute the waveguides 18 throughout the trachea and/or the bronchial tree of the patient. With the waveguides 18 displaced at step 80, the light source 14 can then be turned on at step 64 by the user via the controller 12.

Alternatively or additionally, an EKG signal of the patient and/or an airflow rate through the patient's respiratory tract can be communicated to the controller 12, as described above. In this non-limiting configuration, once the light source 14 is turned on at step 64, the controller 12 can be configured to modulate the light source 14 at step 82. That is, the controller 12 can be configured to turn on and off the light source 14 at specific times during the cardiac cycle of the patient based on the EKG signal, or the controller 12 can be configured to turn on the light source 14 during inhalation and turn off the light source 14 during exhalation as indicated by the airflow rate through the patient's respiratory tract or expansion of the thorax using a circumferential thoracic/abdominal belt volume sensor. In other non-limiting examples, any physiological markers or characteristics including heart rate (i.e., triggering off EKG QRS complex) can be used or combined (e.g., EKG to gate on peak pulmonary artery blood flow and ventilator phase to gate on inhalation) to trigger or gate the modulation of the light source 14 at step 82.

Figure 17:
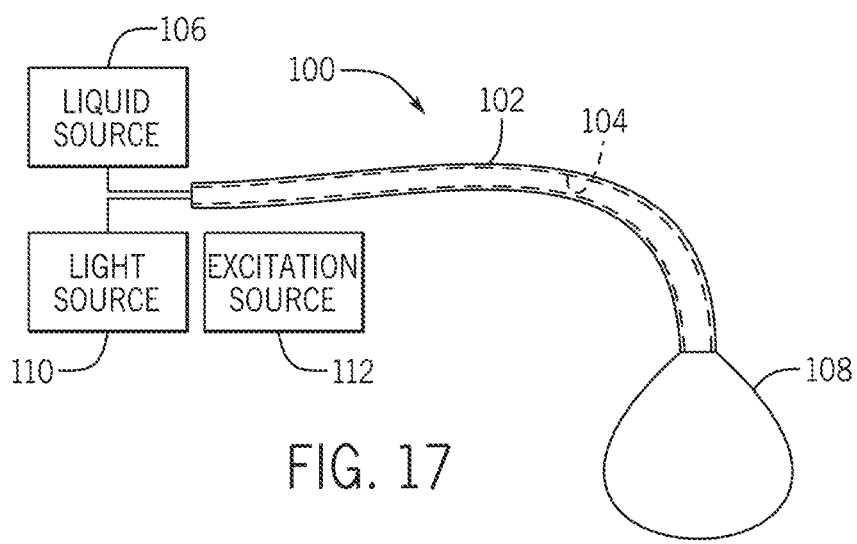
FIG. 17 shows a phototherapy system in accordance with another embodiment of the present disclosure.

FIG. 17 shows another non-limiting example of a phototherapy system 100 for treating or preventing CO poisoning. The phototherapy system 100 includes a tube 102 having a central lumen 104. The central lumen 104 of the tube 102 provides communication between a liquid source 106 and a bag 108. The central lumen 104 also provides communication between a light source 110 and the bag 108. The tube 102 may be fabricated from a flexible, biocompatible material, such as PVC, PTFE, PES, or any other flexible, biocompatible material known in the art. The tube 102 is dimensioned such that a diameter D of the tube 102 is small enough to ensure a patient can breathe (especially not impede exhalation) around the tube 102 if inserted into the patient's esophagus. Alternatively or additionally, the tube 102 can be configured to be inserted into one or more chest (thoracotomy) tubes to place the bag 108 within the pleural spaces surrounding the patient's lungs. In one non-limiting example, the tube 102 can define a diameter D smaller than at least 10 mm.

The liquid source 106 is configured to supply a flow of liquid through the central lumen 104 to the bag 108. The liquid source 106 can be configured to provide water, saline solution, a low light absorption fluid that scatters light, such as lipid emulsions used for feeding IV, or any other biocompatible liquid known in the art. The liquid provided by the liquid source 106 can provide cooling to tissue surrounding the bag 108 and/or can be mixed with the light source 110 to fluidize and diffusely distribute the light source 110 throughout the bag 108. The bag 108 can be fabricated from a collapsible, biocompatible material that is capable of efficiently transmitting the light emitted from the light source 110. The bag 108 and or the tube 102 can be configured such that the bag 108 and/or the tube 102 can fit within a patient's esophagus, within the pleural spaces surrounding the patient's lungs, or within any other portion of the patient's body.

The light source 110 can be a chemiluminescent liquid, a plurality of chemiluminescent particles, a plurality of phosphorescent particles, a laser, or a LED. It is well known in the art that the reactants of a photochemical reaction can be chosen to produce a chemiluminescent liquid/particle that emits light at a desired wavelength. Therefore, if the light source 110 is a chemiluminescent liquid or particle, the chemiluminescent liquid/particles can comprise reactants that produce a photochemical reaction that emits light at a wavelength between approximately 590 nm and 650 nm. In other non-limiting examples, the chemiluminescent liquid/particles can comprise reactants that produce a photochemical reaction that emits light at a wavelength between approximately 390 nm and approximately 690 nm. In still other non-limiting examples, the chemiluminescent liquid/particles is composed reactants that produce a photochemical reaction that emits light at any wavelength absorbed by COHb.

Typically, phosphorescent particles include a dopant ion (also commonly referred to as a phosphor) that is doped into a host lattice. The dopant ion is excited by an outside source (e.g., light radiation) to an upper excited state and, upon relaxation back to its ground state, the dopant ion emits light at a given wavelength. Phosphorescent particles are of particular interest because they are typically chemically inert and can convert absorbed excitation energy into emitted light with quantum efficiencies near one-hundred percent. It is well known in the art that the dopant ion, the host lattice, the crystal structure of the host lattice, the excitation source, and the concentration of the dopant ion within the host lattice, among other things, can influence the wavelength of light emitted by a phosphorescent particle. Therefore, if the light source 110 includes phosphorescent particles, the phosphorescent particles can comprise a dopant ion and host lattice that emit light at a wavelength between approximately 590 nm and approximately 650 nm, when excited by an excitation source 112. In other non-limiting examples, the phosphorescent particles can comprise a dopant ion and host lattice that emit light at a wavelength between approximately 390 nm and approximately 690 nm, when excited by the excitation source. In still other non-limiting examples, the phosphorescent particles can comprise a dopant ion and host lattice that emit light at a any wavelength absorbed by COHb, when excited by the excitation source.

If the light source 110 includes phosphorescent particles, the phototherapy system 100 can include the excitation source 112 configured to activate the phosphorescent particles and cause the phosphorescent particles to emit light at the desired wavelength. The excitation source 112 can be a laser, a lamp, one or more LED's, or any viable excitation source capable of activating the phosphorescent particles.

As described above, the liquid source 106 can be configured to provide a low absorption fluid that scatters light. In this non-limiting example, the low absorption fluid can be configured to transmit and scatter light emitted by the light source 110. The light source 110 can be a laser coupled to a waveguide, such as an optical fiber, which is placed inside the bag 108. The bag 108 filled with the low absorption fluid could serve as a diffuser of the light generated by the laser and transmitted to the bag 108 within the patient's pleural spaces or any other body cavity.

Figure 18:
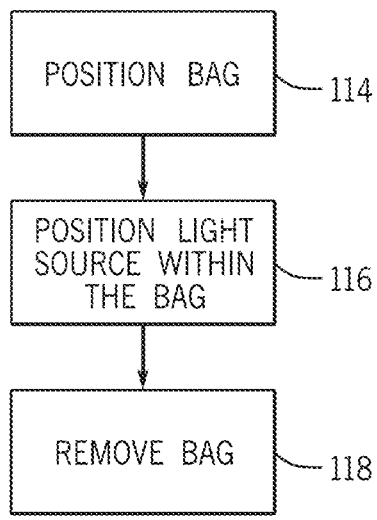
FIG. 18 outlines the steps for operating the phototherapy system of FIG. 17 in accordance with one embodiment of the present disclosure.

One non-limiting example of operation of the phototherapy system 100 will be descried with reference to FIGS. 17 and 18. In operation, a user of the phototherapy system 100 can treat a patient with CO poisoning. The steps the user can perform to treat the patient with CO poisoning are illustrated in FIG. 18. The user of the phototherapy system 100 is, typically, a trained healthcare professional. It should be known that following description of the treatment of CO poisoning using the phototherapy system 100 is one exemplary non-limiting example and, as will be recognized by one of skill in the art, alternative methods or different steps may be used.

As shown in FIG. 18, first, the bag 108 may be positioned at step 114 by the user such that the bag 108 is positioned within a portion of the patient's body. As described above, the portion of the patient's body can include the esophagus, the pleural spaces, or any other part of the body. Following the positioning 114 of the bag 108, the light source 110 can then be fluidly communicated at step 116 into the bag 108 via the central lumen 104. Alternatively or additionally, the liquid from the liquid source 106 can be fluidly communicated at step 116 into the bag 108 via the central lumen 104. Once the light source 110 is within the bag 108, the light output from the light source 110 transmits through the bag 108 and emits onto the portion of the patient's body. As described above, the light source 110 can be configured to output light at a wavelength between 590 nm and 650 nm which are wavelengths that are capable of penetrating into, or through, human tissue and being absorbed by COHb. Therefore, whether the bag 108 is positioned within the esophagus, or pleural spaces of the patient, the light emitted from the light source 110 penetrates through the surrounding tissue to reach the pulmonary vasculature of the patient. When the light emitted from the light source 110 reaches the pulmonary vasculature, the emitted light is absorbed by COHb thereby photodissociating the CO from the Hb. Since the alveolar partial pressure of oxygen is much greater that the partial pressure of CO in the pulmonary vasculature, the oxygen pressure gradient drives oxygen molecules to bind to deoxygenated Hb at a far greater rate than CO. Thus, the CO is photodissociated from COHb into the alveolus of the patient and exhausted during exhalation.

The bag 108, which can be thin walled and transparent, can be left within the portion of the patient's body for a predetermined amount of time to ensure that a desired amount of phototherapy is provided and the irradiated tissue is not damaged. Once the bag 108 has been within the portion of the patient's body for the predetermined amount of time, the user can then remove the bag 108 at step 118 from within the portion of the patient's body.

Alternatively or additionally, the light source 110 can include phosphorescent particles, as described above. In this non-limiting example, before the light source 110 is fluidly communicated into the bag 108 at step 116, the light source 110 can be activated by the excitation source 112.

It should be appreciated that, in other non-limiting examples, the bag 108 may not be necessary to provide a barrier between the light source 110 the portion of the patient's body. That is, in some non-limiting examples, the light source 110 may be a non-toxic, chemiluminescent fluid that can be infused into, for example, the pleural space of the patient to provide a better distribution of light emission from the light source 110. Following the desired duration of phototherapy provided by the light source 110, the light source can be removed, for example, via suction.

Figures 19, 20:
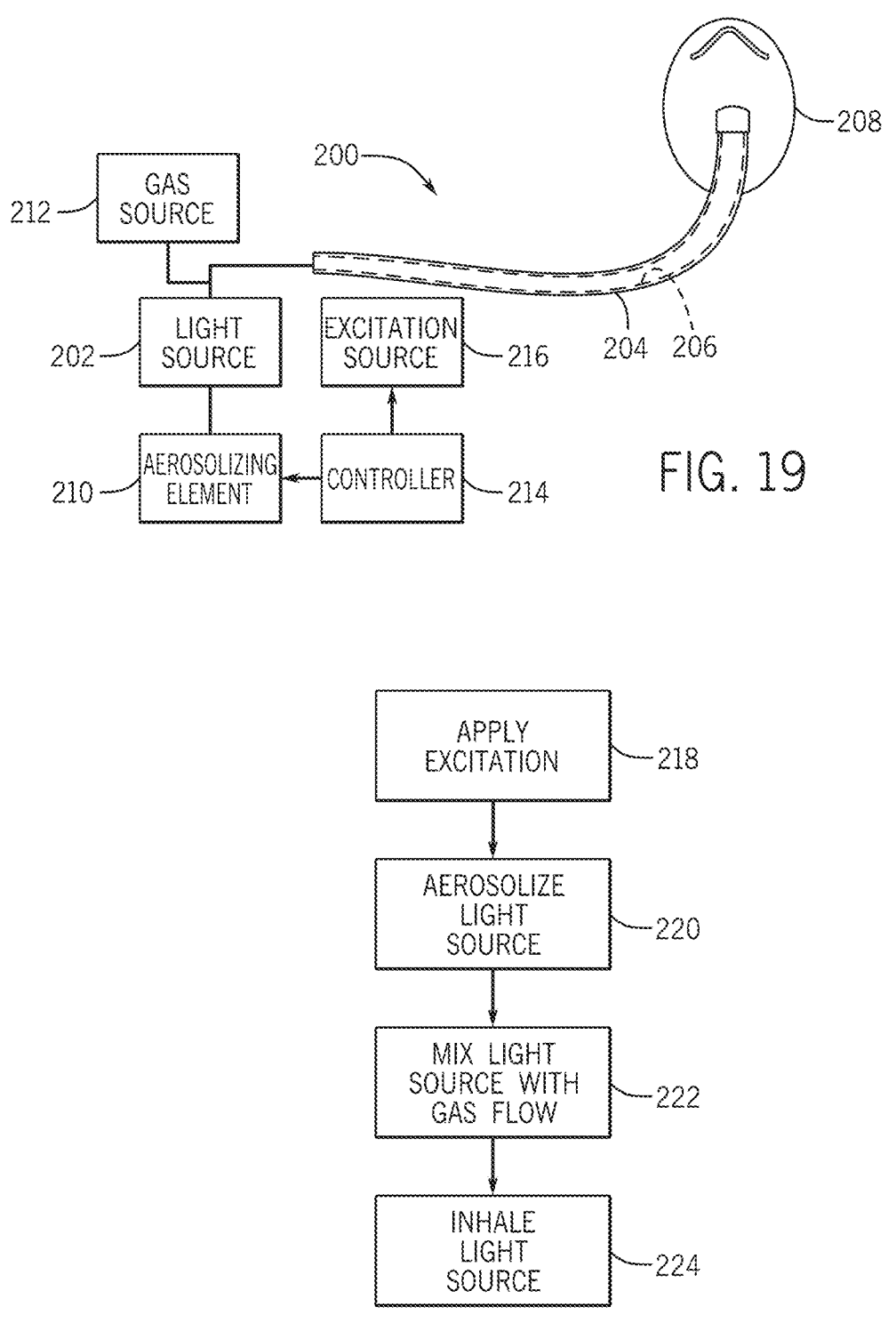

FIG. 19 shows another non-limiting example of a phototherapy system 200 for treating or preventing CO poisoning. The phototherapy system 200 includes a light source 202 and a tube 204 having a central lumen 206. The tube 204 is configured to provide communication between the light source 202 and an airway 208. The illustrated airway 208 is in the form of a mask; however, in other non-limiting examples, the airway 208 may be in the form of any device configured to provide communication to the lungs of the patient. That is, in other non-limiting examples, the airway 208 may be in the form of an endotracheal tube, nasal prongs, or a tracheostomy tube, to name a few. Alternatively or additionally, the airway 208 can be any mask, or respirator, known in the art which covers at least one of a patient's nose and mouth. For example, the airway 208 can be a respirator typically worn by firemen and/or military personnel. The tube 204 may be fabricated from a flexible, biocompatible material, such as PVC, PTFE, PES, or any other flexible, biocompatible material known in the art. Alternatively or additionally, the tube 204 can be connected to an endotracheal tube.

The light source 202 may comprise a plurality of phosphorescent particles. The phosphorescent particles of the light source 202 comprise a dopant ion and host lattice that emit light at a wavelength between approximately 590 nm and approximately 650 nm, when excited by an excitation source 216. Additionally, the phosphorescent particles of the light source 202 are chemically inert and non-toxic to human beings. In other non-limiting examples, the phosphorescent particles can comprise a dopant ion and host lattice that emit light at a wavelength between approximately 390 nm and approximately 690 nm, when excited by the excitation source 216. In still other non-limiting examples, the phosphorescent particles can comprise a dopant ion and host lattice that emit light at a any wavelength absorbed by COHb, when excited by the excitation source 216.

The phosphorescent particles of the light source 202 can define varying particle diameters such that the phosphorescent particles, when inhaled by a person, come to rest in locations throughout the trachea and bronchial tree. Additionally or alternatively, the phosphorescent particles can be coated with an adhesive that adheres the phosphorescent particles to mucus and/or tissue within the trachea or bronchial tree of a person.

As shown in FIG. 19, the light source 202 is also in communication with an aerosolizing element 210 and a gas source 212. The aerosolizing element 210 is configured to aerosolize the phosphorescent particles thereby enabling the phosphorescent particles mix with a flow of fluid provided by the gas source 212 and flow through the central lumen 206 of the tube 204 and into the airway 208. The aerosolizing element 210 may also configured to aerosolize a specific number of phosphorescent particles such that a particle load inhaled by a person would not cause significant damage to the person's lungs (biologically inert particles which are not bioreactive). The aerosolizing element 210 can be a nebulizer, a fluidized bed, or any other viable aerosolizing device known in the art. The gas source 212 can be a pressurized source of air or oxygen. The aerosol size can be engineered by size to target the portion of the lung most useful to produce CO exhalation during poisoning. For example, 1-2 micron particles for targeting the alveoli, 5-10 micron particles to lodge in terminal bronchi, which are close to the pulmonary arterial supply to alveoli.

A controller 214 is in communication with the aerosolizing element 210 and the excitation source 216. The controller 214 is configured to control when the aerosolizing element 210 aerosolizes the light source 202 and when the excitation source 216 activates the light source 202. The excitation source 216 can be a laser, a lamp, one or more LED's, or any viable excitation source capable of activating the light source 202.

One non-limiting example of operation of the phototherapy system 200 will be descried with reference to FIGS. 19 and 20. In operation, the phototherapy system 200 can treat a person with CO poisoning or be used to prevent CO poisoning with a person in an atmosphere with an elevated CO concentration. The steps for treating or preventing CO poisoning using the phototherapy system 200 are illustrated in FIG. 20. It should be known that following description of the treatment or prevention of CO poisoning using the phototherapy system 200 is one exemplary non-limiting example and, as will be recognized by one of skill in the art, alternative methods or different steps may be used.

As shown in FIG. 20, first, the phosphorescent particles of the light source 202 may be activated at step 218 via the controller 214 instructing the excitation source 216 to turn on. Once the phosphorescent particles of the light source 202 are is activated at step 218, the controller 214 then instructs the aerosolizing element 210 to aerosolize the phosphorescent particles at step 220. The aerosolized phosphorescent particles are then mixed at step 222 with a fluid flow from the gas source 212 which enables the aerosolized phosphorescent particles to flow into the central lumen 206 of the tube 204. As described above, the aerosolized element 210 can be configured to control the particle load of the phosphorescent particles within the central lumen 206 such that, when inhaled by a person, the particle load would not cause significant damage to a person's lungs.

Once the aerosolized phosphorescent particles are mixed at step 222 with the fluid flow from the gas source 212 and begin to flow into the central lumen 206, a person wearing the airway 208 could inhale the aerosolized light source 202 at step 224 causing the phosphorescent particles of the light source 202 to scatter throughout the person's trachea and bronchial tree. As described above, the phosphorescent particles, once activated, can be configured to output light at a wavelength between 590 nm and 650 nm, which are wavelengths that are capable of penetrating into, or through, human tissue and being absorbed by COHb. Therefore, the light emitted from the phosphorescent particles scattered throughout the person's trachea and bronchial tract can penetrate through the surrounding tissue to reach the pulmonary vasculature of the person. When the light emitted from the phosphorescent particles reaches the pulmonary vasculature, the emitted light is absorbed by COHb thereby photodissociating the CO from the Hb. Since the alveolar partial pressure of oxygen is much greater that the partial pressure of CO in the pulmonary vasculature, the oxygen pressure gradient drives oxygen molecules to bind to deoxygenated Hb at a far greater rate than CO. Thus, the CO is photodissociated from COHb into the alveolus of the person and removed from the body by exhalation.

It should also be known that the light source 202, when inhaled, can reach the person's alveoli and, therefore, the thickness of tissue to be penetrated will be very small (e.g., less than 1-5 microns). In this non-limiting example, the phosphorescent particles can be configured to output light at a wavelength between 390 nm and 750 nm.

Alternatively or additionally, the phosphorescent particles can be nano-sized particles, such as lipid nanoparticles (e.g., inhaled amikacin antibiotics, or rhodamine S lipid nanoparticles), which, when injected, or inhaled, are configured to localize in the lungs. In this non-limiting example, the phosphorescent particles can be configured to output light at any wavelength absorbed by COHb, as no penetration of tissue would be needed.

As mentioned above the phototherapy system 200 can be used to prevent CO poisoning. This non-limiting application, can be directed towards, for example, military personnel or firemen, who can be required to perform in atmospheres with elevated CO concentrations. In one non-limiting example, the phototherapy system 200 can be integrated into a respirator used by military personnel or firemen. Additionally, the phototherapy system 200 can include a measurement device, for example a transcutaneous COHb pulse oximeter, capable of continuously measuring the arterial CO concentration in a person's blood, and the controller 214 can be configured to aerosolize the light source 202 via the aerosolizing element 210 in response to measuring an elevated CO concentration in the person's blood.

Examples

The following examples set forth, in detail, ways in which the phototherapy systems described herein may be used or implemented, and will enable one of skill in the art to more readily understand the principle thereof. The following examples are presented by way of illustration and are not meant to be limiting in any way.

Mice Studies

Mice were anesthetized with an intraperitoneal (i.p.) injection of ketamine (120 mg·kg$^{-1}$) and fentanyl (0.9 mg·kg$^{-1}$). Following a tracheotomy, rocuronium (1 mg·kg$^{-1}$) was injected i.p. to induce muscle relaxation. Volume-controlled ventilation was provided at a respiratory rate of 90 breaths·min$^{-1}$, a tidal volume of 10 ml·kg$^{-1}$ and a positive end expiratory pressure (PEEP) of 1 cm H$_2$O. Catheters were placed in the carotid artery and jugular vein; then mice underwent a median thoracotomy to expose the lungs.

Mice were poisoned by breathing 400 ppm CO in air. Inhaled and exhaled CO concentrations were measured using a CO analyzer (MSA Altair-PRO; MSA Safety Inc., Pittsburgh, PA). In some experiments, mice were poisoned by breathing 2000 ppm CO in air and CO concentration was measured using an infra-red CO gas analyzer (MIR2M; Altech-Environment, Geneva, IL). The percentage of COHb in arterial blood was sampled and measured during and after CO poisoning and COHb half-life was calculated.

Light at 532 and 690 nm wavelength was generated by an Aura KTP laser (American Medical Systems, Minnetonka, MN) and a prototype laser (Syneron-Candela, Wayland, MA) respectively. Light at 570, 592 and 628 nm wavelength was generated by Visible Fiber Lasers (VFL-P lasers, MPB Communications Inc., Montreál, Canada). The power of the light irradiating the lungs was measured with a power meter (Thorlabs Inc., Dachau, Germany). The light irradiance was calculated as I=Power (W)/Area (cm$^2$). The radiant exposure was calculated as RE (J·cm$^{-2}$)=I (W·cm$^{-2}$)·t (sec) where RE is radiant exposure, I is irradiance and t is the time of exposure.

A 1 mm diameter optical fiber with a 1.2 cm long diffusing tip, which emits light at 360 degrees, was placed via the oropharynx into the esophagus of anesthetized and mechanically ventilated mice. Intermittent phototherapy with light at 532 nm was tested. The power was set to 1.5 W and light was pulsed at 1 Hz with a 200 ms pulse width.

Statistical analysis was performed using Sigma Plot 12.5 (SPPS, Inc., Chicago, IL). Data were analyzed using Student's t-test and a one-way ANOVA with post hoc Bonferroni test (two-tailed). Two Way ANOVA for repeated measurements was used to compare variables over time between groups. For survival analyses, Kaplan-Meier estimates were generated and compared using the log-rank test. Statistical significance was defined as a p value of less than 0.5. All data are expressed as mean±SD unless specified otherwise.

To investigate whether visible light might be used to dissociate CO from hemoglobin in vivo, a murine model of CO poisoning was developed. Anesthetized and mechanically ventilated mice were poisoned by inhaling 400 parts per million (ppm) CO in air for one hour and subsequently treated by breathing either air or 100% O$_2$. The exhaled CO concentration was continuously monitored and the CO uptake and elimination rates were determined. During CO poisoning and subsequent treatment periods, COHb concentration in arterial blood was measured sequentially and the COHb-$t_{1/2}$ was calculated.

Figure 21A:
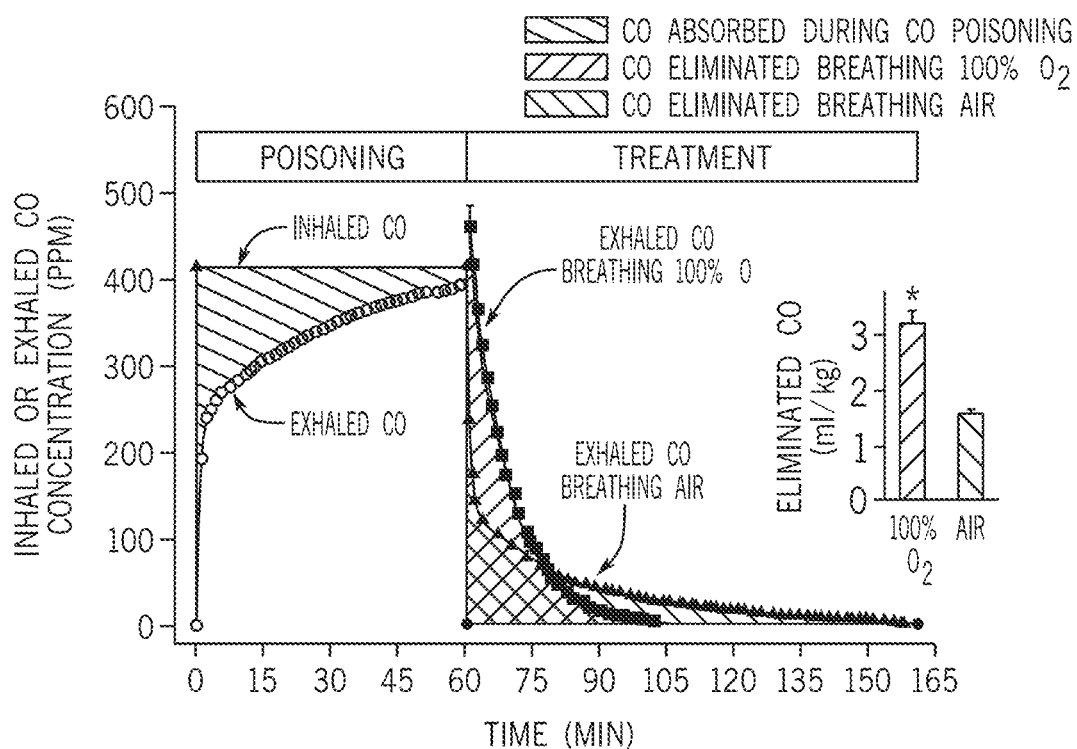
FIG. 21A shows inhaled or exhaled carbon monoxide concentration versus time for a murine model of carbon monoxide poisoning.

The area under the curve (AUC) of exhaled CO concentration during the treatment period represents the eliminated quantity of CO. The exhaled CO concentration during the first 15 minutes of breathing 100% O$_2$ was significantly greater than the first 15 minutes of breathing air, indicating that a larger amount of CO was eliminated during this period (AUC: 3568±242 vs.1744±101, p<0.001), as shown in FIG. 21A. In contrast, after approximately 20 minutes of treatment, the exhaled CO concentration was significantly higher in air-breathing mice, demonstrating the presence of a larger amount of CO remaining for elimination (AUC: 858±41 vs. 275±49, p<0.001).

Figure 21B:
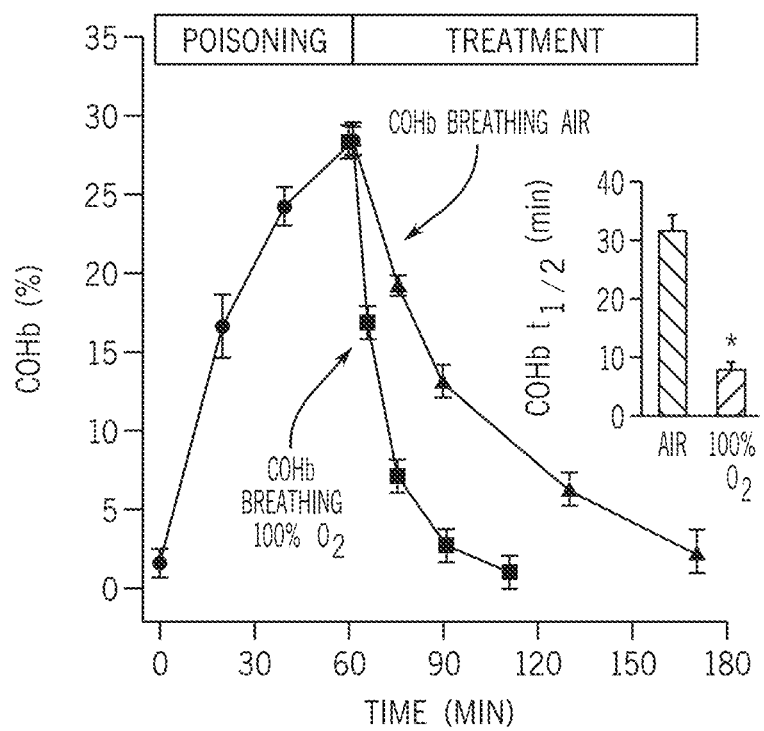
FIG. 21B shows carboxyhemoglobin percentage versus time for a murine model of carbon monoxide poisoning.

At the end of the one-hour poisoning period, 28.0±0.6% (mean±SD) of circulating hemoglobin was saturated with CO. Treatment by ventilation with 100% O$_2$ decreased COHb concentration faster than treatment with air (COHb-$t_{1/2}$: 8.2±1.2 vs. 31.5±3.1 min, p<0.001), as shown in FIG. 21B. In this murine model, both the exhaled CO concentration and arterial COHb levels reflect the advantage of breathing 100% $O_2$ over breathing air after CO poisoning.

Figure 22:
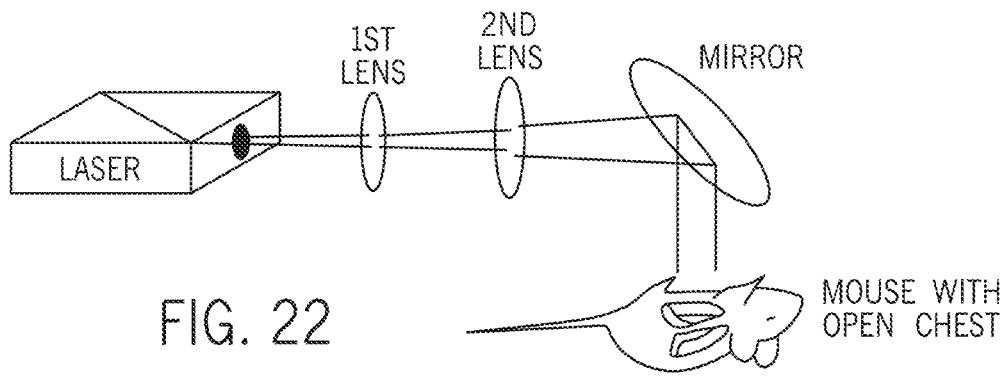
FIG. 22 shows a phototherapy system applying laser light directly to the lungs of a mouse in accordance with one embodiment of the present disclosure.

To evaluate the effect of direct illumination of lungs on the CO elimination rate, anesthetized and mechanically ventilated mice were subjected to a median sternotomy to expose both lungs. After breathing 400 ppm CO for one hour, the mice were treated by ventilation with either air or 100% $O_2$, with or without phototherapy at 628 nm wavelength ($\lambda$) and 54 mW·cm$^{-2}$ irradiance. The test setup for these studies is shown in FIG. 22.

Figure 23A:
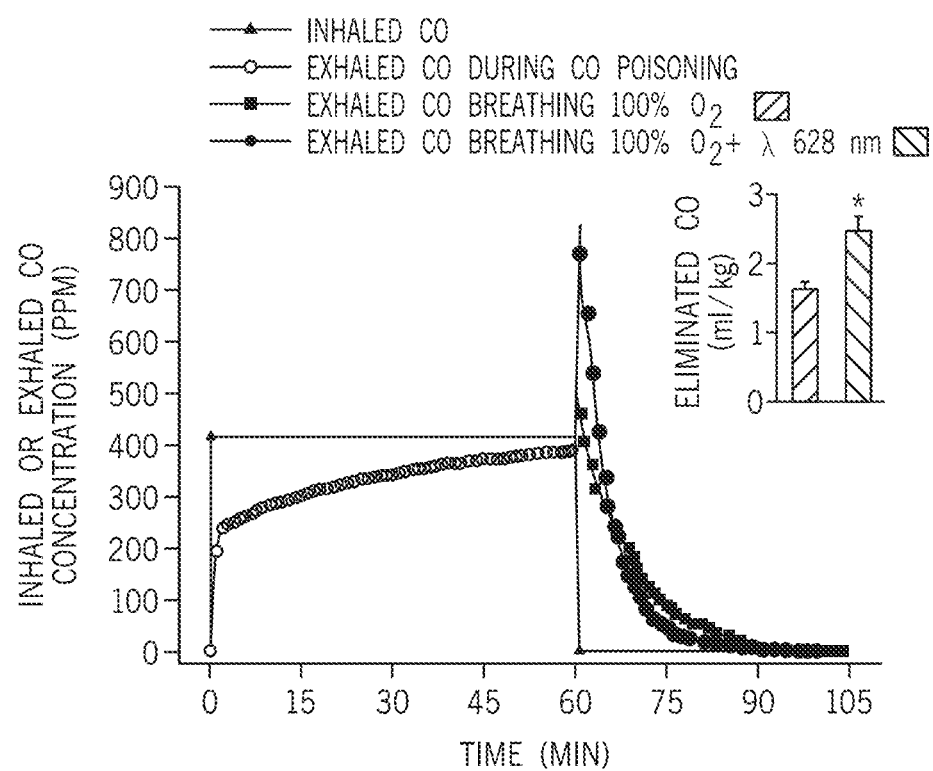
FIG. 23A shows inhaled or exhaled carbon monoxide concentration versus time during phototherapy on mice breathing either air or 100% oxygen poisoned with 400 ppm CO for one hour.
Figure 23B:
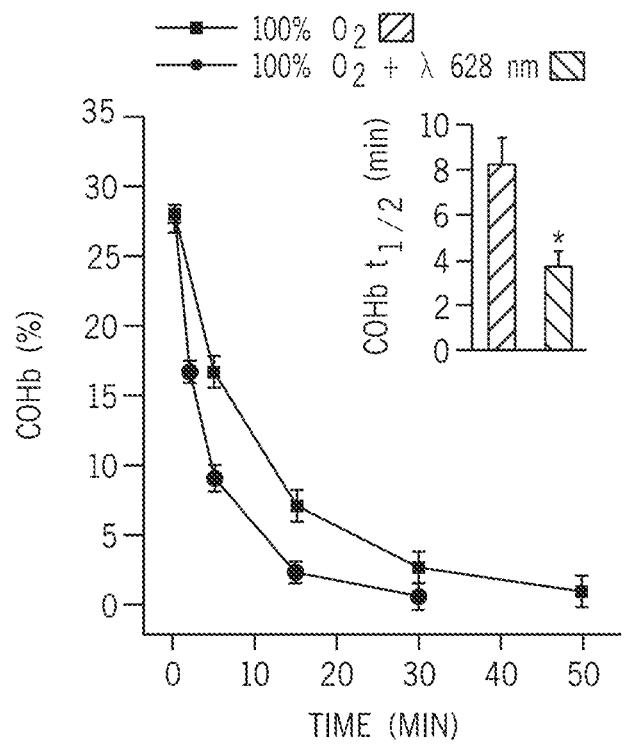
FIG. 23B shows carboxyhemoglobin percentage versus time during phototherapy on mice breathing 100% oxygen poisoned with 400 ppm CO for one hour.

Pulmonary phototherapy added to 100% 02 breathing induced a dramatic increase of exhaled CO concentration during the first 5 minutes of treatment, indicating greater CO elimination (AUC: 2763±215 vs. 1904±106; p<0.001), as shown in FIG. 23A. Commencing at 8 minutes of treatment, exhaled CO levels were significantly higher in mice treated with 100% $O_2$ alone as compared with light and 100% $O_2$, demonstrating the presence of a larger amount of CO remaining to be eliminated in the former. The reduction of blood COHb concentration during treatment with 100% $O_2$ and phototherapy was greater than treatment with 100% $O_2$ alone, and the COHb-$t_{1/2}$ was significantly shorter (3.8±0.5 vs. 8.2±1.2 min, p<0.001), as shown in FIG. 23B.

Figure 23C:
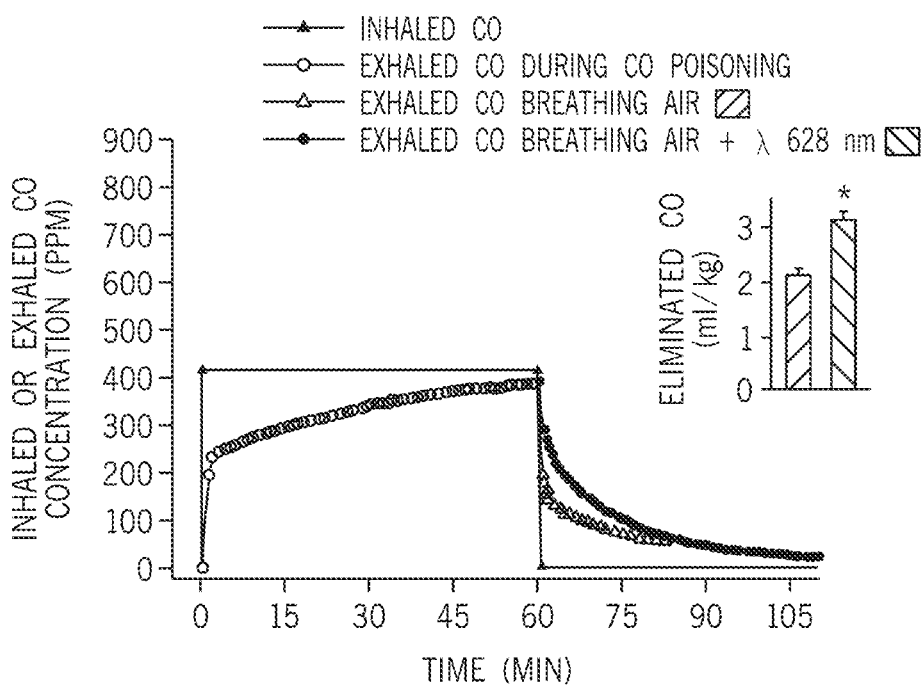
FIG. 23C shows inhaled or exhaled carbon monoxide concentration versus time during phototherapy on mice breathing air poisoned with 400 ppm CO for one hour.
Figure 23D:
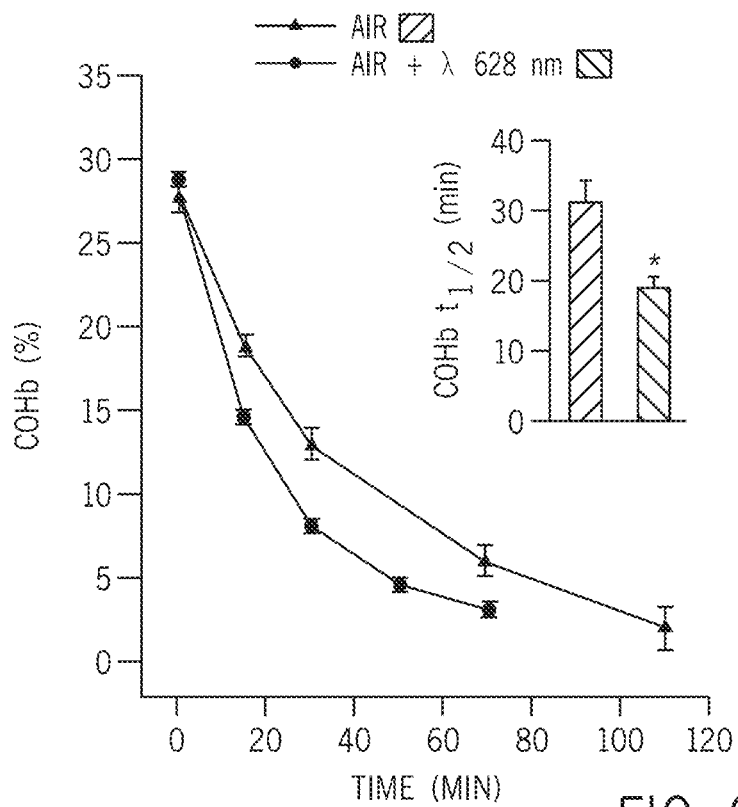
FIG. 23D shows carboxyhemoglobin percentage versus time during phototherapy on mice breathing air poisoned with 400 ppm CO for one hour.
Figure 24A:
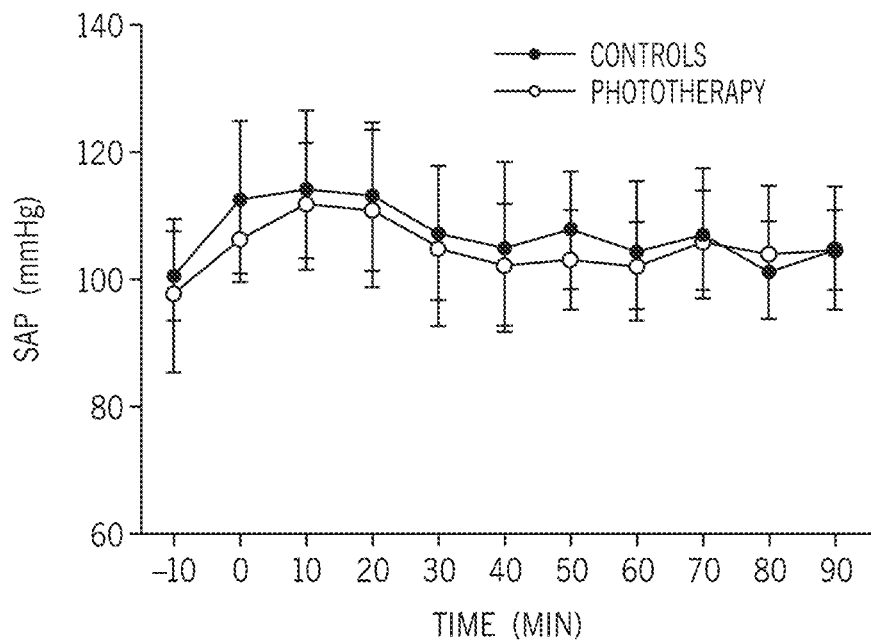
FIG. 24A shows systolic arterial pressure versus time for mice with and without phototherapy at 628 nm.
Figure 24B:
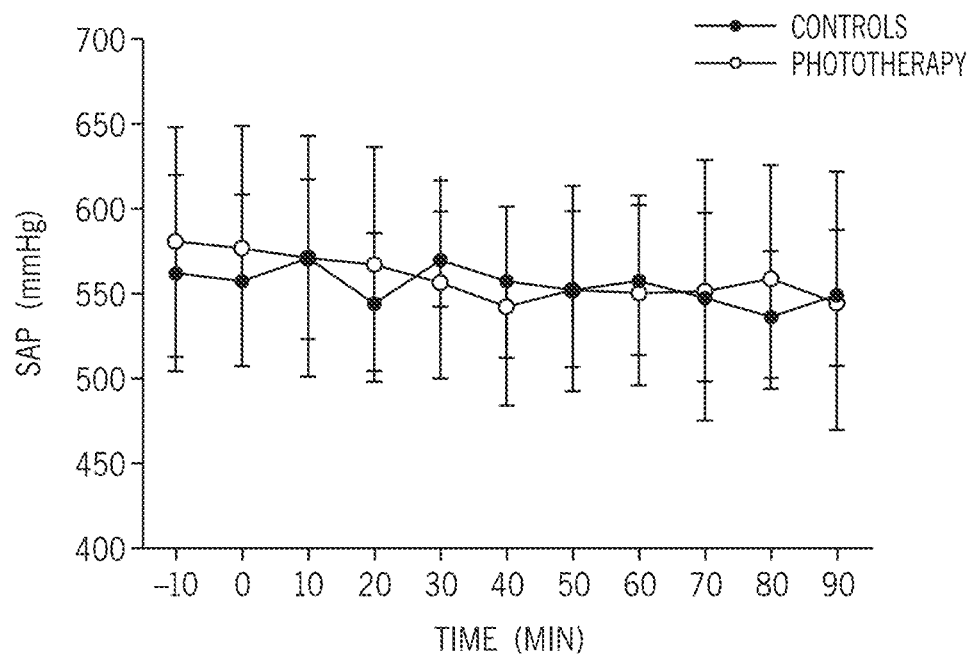
FIG. 24B shows heart rate versus time for mice with and without phototherapy at 628 nm.
Figure 25:
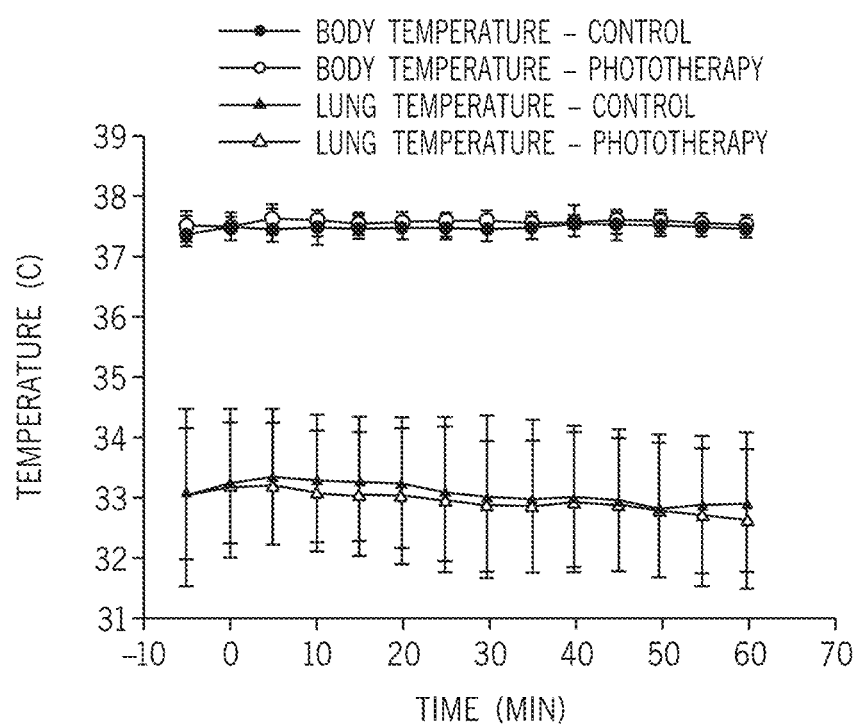
FIG. 25 shows the effect of phototherapy at 628 nm on mice body and lung temperature.

To evaluate the efficacy of phototherapy in the presence of a lower concentration of inspired $O_2$, whether lung phototherapy could increase the CO elimination rate while mice were breathing air was tested. Phototherapy added to air breathing was associated with an increased quantity of CO eliminated during the first 25 minutes of treatment (AUC: 3451±175 vs. 2359±130, p<0.001), as shown in FIG. 23C, and COHb-$t_{1/2}$ was significantly shorter (19.2±1.3 vs. 31.5±3.1 min, p<0.001), as shown in FIG. 23D. There was not a significant difference in systemic arterial pressure, heart rate, rectal or lung surface temperature between mice treated with or without phototherapy, as shown in FIGS. 24A, 24B, and 25. These results show that after CO poisoning, direct lung phototherapy increased the rate of CO elimination in mice breathing either 100% $O_2$ or air.

Figure 26A:
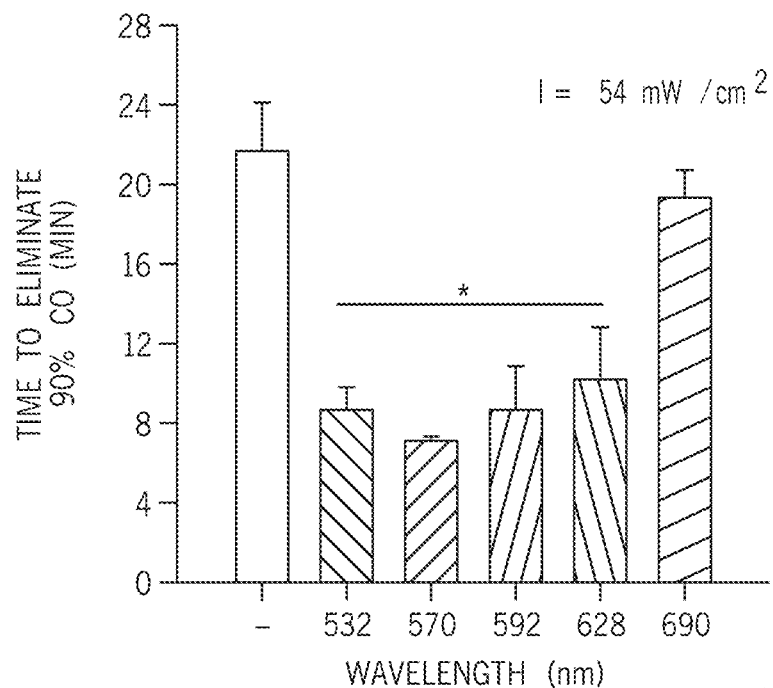
FIG. 26A shows the effect of wavelength on the time to eliminate 90% carbon monoxide.

To test whether visible light at different wavelengths could dissociate COHb in vivo, mice were poisoned with CO and treated with phototherapy using light at 532, 570 (green), 592 (yellow) or 628 (red) nm. To exclude non-specific effects of lung illumination on the CO elimination rate, light at 690 nm (infra-red), which does not dissociate COHb in vitro was also tested. Mice were anesthetized, mechanically ventilated, subjected to a midline thoracotomy and then poisoned with 400 ppm CO for 5 minutes followed by 25 minutes of treatment with 100% $O_2$, either alone or together with phototherapy at each chosen wavelength. The CO elimination rate was determined by calculating the time necessary to eliminate 90% of the CO absorbed during the poisoning period ($T_{90\%}CO$). Phototherapy at 532, 570, 592 or 628 nm, when added to 100% $O_2$ treatment, significantly decreased the $T_{90\%}CO$ when compared to 100% $O_2$ alone (respectively 8.7±1.2, 7.2±0.2, 8.8±2.2, 10.2±2.7 vs. 21.8±2.4 min, each comparison p<0.005), as shown in FIG. 26A. In contrast, phototherapy at 690 nm did not decrease the $T_{90\%}CO$ when compared to 100% $O_2$ breathing alone (19.4±1.5 vs. 21.8±2.4 min, p=0.892). These results show that phototherapy at wavelengths between 532 and 628 nm improves CO elimination rate in CO-poisoned mice.

Figure 26B:
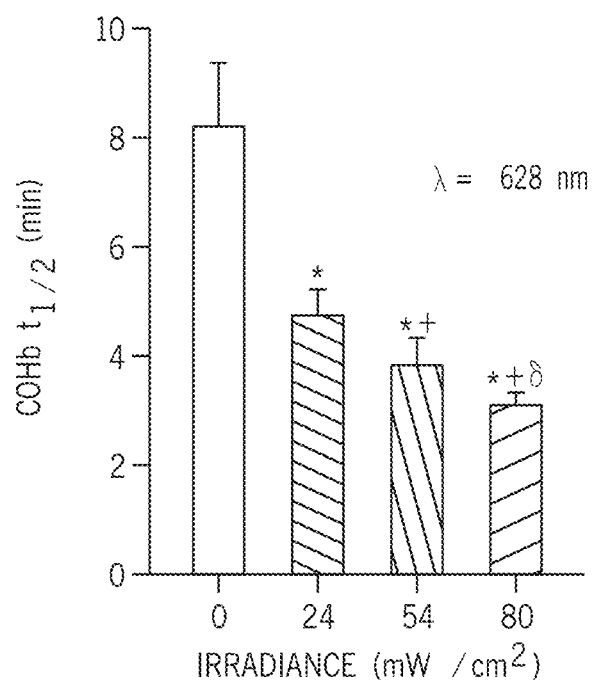
FIG. 26B shows carboxyhemoglobin half-life versus irradiance at 628 nm.

To investigate the relationship between the light energy and the COHb photodissociation efficiency, mice were poisoned with CO and treated with 100% $O_2$ combined with continuous phototherapy at 628 nm using either a low, medium or high power (irradiance=24, 54 and 80 mW·cm$^{-2}$). Each of these three energy levels decreased blood COHb-$t_{1/2}$ as compared to mice treated by breathing 100% $O_2$ alone (4.8±0.5, 3.8±0.5, 3.1±0.2 vs. 8.2±1.2 min, each comparison p<0.001), as shown in FIG. 26B. The results show that continuous phototherapy with an irradiance as low as 24 mW·cm$^{-2}$ effectively increased the rate of CO elimination. Moreover, the reduction in COHb-$t_{1/2}$ obtained with phototherapy was enhanced with the increase of the energy of incident light.

Figure 26C:
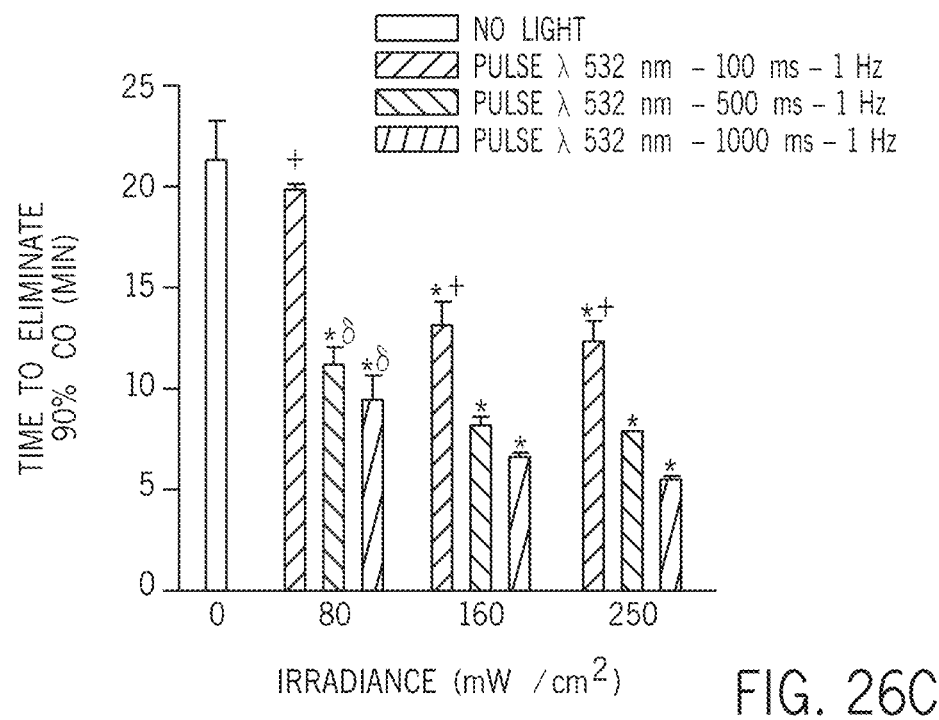
FIG. 26C shows the effect of pulse duration and irradiance on the time to eliminate 90% carbon monoxide.

Heat produced by continuous irradiation might damage the lung. One approach to reduce tissue heating is to administer the light intermittently. To investigate the effect of intermittent phototherapy on the CO elimination rate, mice were poisoned with 400 ppm CO for 5 minutes followed by 25 minutes of treatment with 100% $O_2$ alone or with light at three energy levels (80, 160 and 250 mW·cm$^{-2}$) and three different pulse widths (100, 500, 1000 msec) at a constant frequency of 1 Hz. When using light at 80 mW·cm$^{-2}$ and with a pulse width of 100 msec, $T_{90\%}CO$ was not decreased when compared to breathing 100% $O_2$ alone, as shown in FIG. 26C. At each energy level, the longer the pulse the greater was the reduction in $T_{90\%}CO$. At each pulse width tested, $T_{90\%}CO$ was reduced when the irradiance was increased from 80 to 160 mW·cm$^{-2}$. There was no further reduction when the irradiance was increased to 250 mW·cm$^{-2}$. These results show that intermittent phototherapy can also improve the rate of CO elimination, although the effect is less than continuous phototherapy.

Figure 26D:
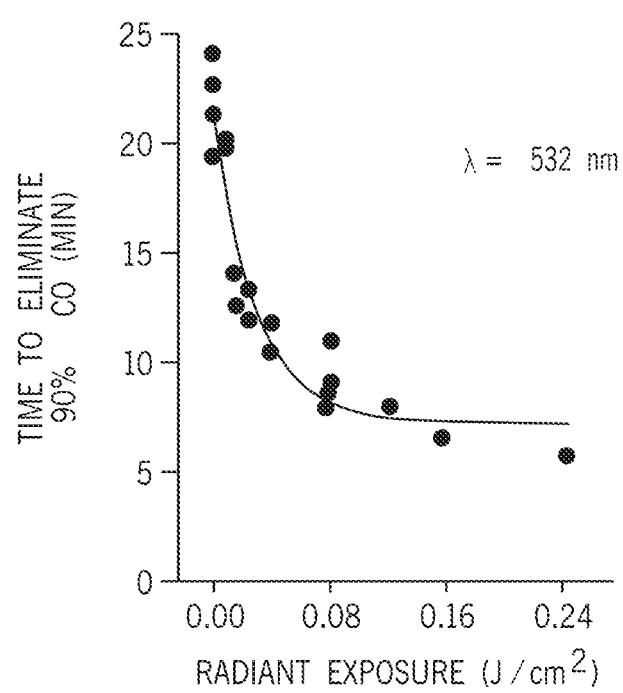
FIG. 26D shows time to eliminate 90% carbon monoxide versus radiant exposure at 532 nm.

To evaluate the combined effects of pulse width and light irradiance on the CO elimination rate, the radiant exposure for each treatment was calculated. The relationship between the CO elimination rate and the radiant exposure is described by a three parameter exponential decay curve ($R^2$=0.93, p<0.0001) shown in FIG. 26D. As shown in FIG. 26D, when the radiant exposure is greater than 0.8 J·cm$^{-2}$, a plateau is reached, and a further increase of either power or pulse duration does not increase the CO elimination rate.

Figure 27A:
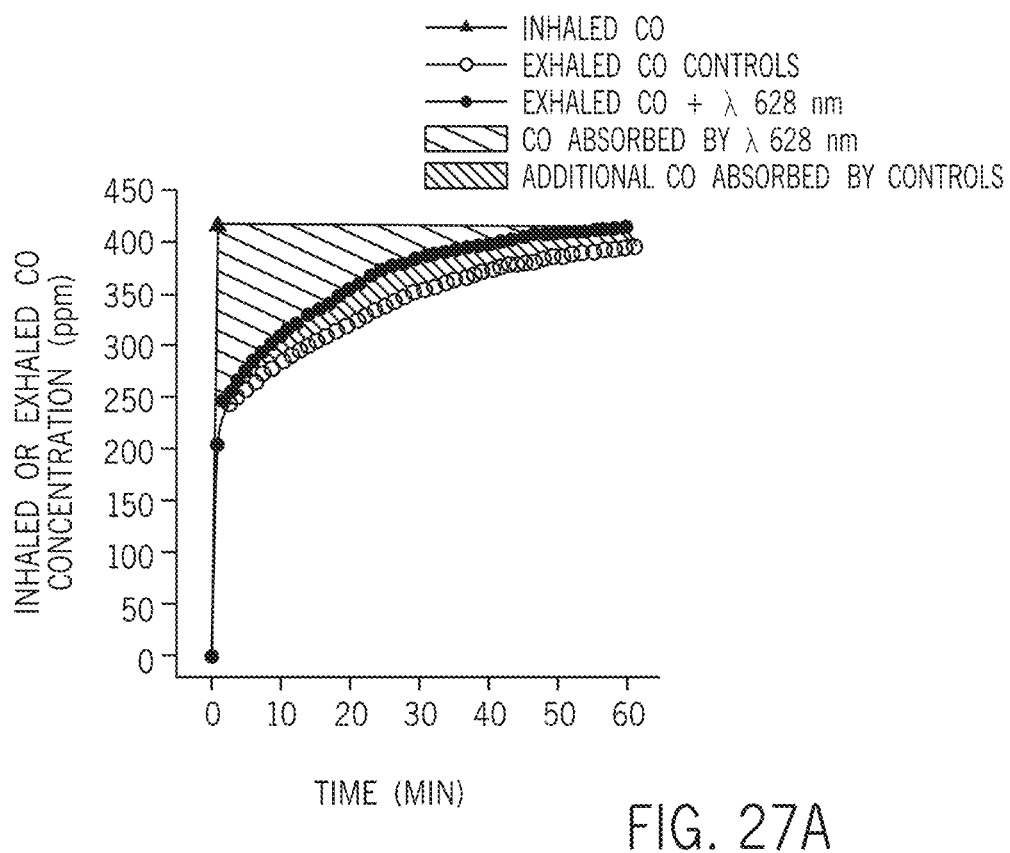
FIG. 27A shows inhaled and exhaled carbon monoxide concentrations versus time for mice with or without simultaneous phototherapy.
Figure 27B:
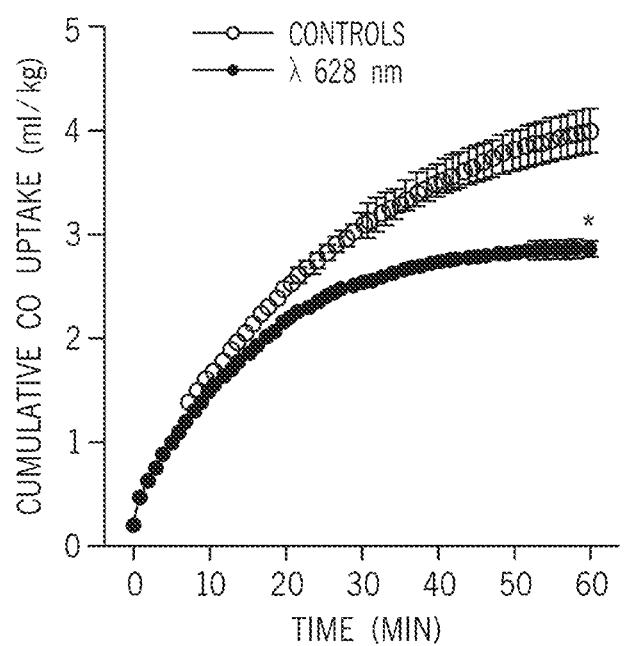
FIG. 27B shows cumulative carbon monoxide uptake versus time for mice with or without simultaneous phototherapy.
Figure 27C:
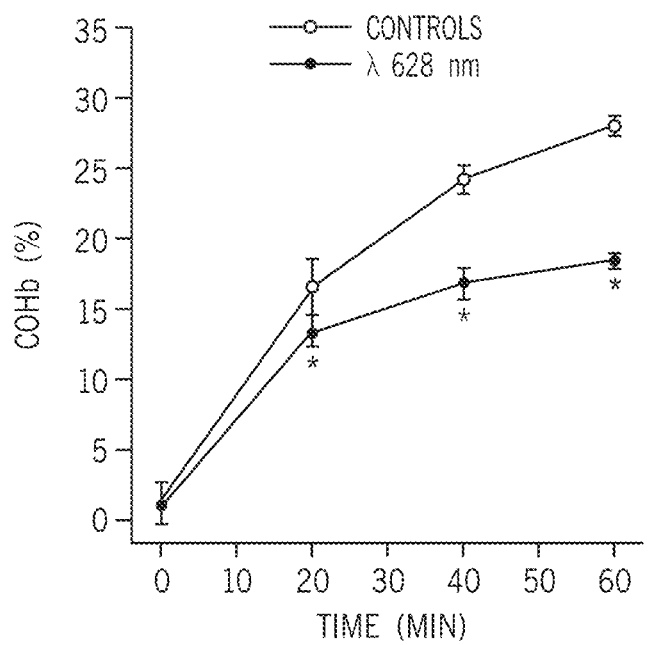
FIG. 27C shows carboxyhemoglobin percentage versus time for mice with or without simultaneous phototherapy.

To test whether phototherapy might prevent CO poisoning during CO exposure, anesthetized and mechanically ventilated mice were exposed to 400 ppm CO in air for one hour with or without simultaneous direct lung phototherapy at 628 nm. The exhaled CO concentration was significantly greater in mice treated with phototherapy during the poisoning, as shown in FIG. 27A, and the amount of CO absorbed by these mice was significantly less than control mice (0.134±0.005 vs.0.189±0.11 umol·g$^{-1}$, p<0.001), as shown in FIG. 27B. In mice receiving phototherapy during CO exposure, arterial blood COHb levels at 20, 40 and 60 minutes were significantly lower than in controls (13.4±1.1 vs. 16.5±1.9, 16.8 1.1 vs. 24.2±1.2, 18.4±0.6 vs. 28.0±0.6% respectively, p<0.001), as shown in FIG. 27C. These results show that direct lung illumination during ongoing CO exposure is associated with reduced CO absorption and lower arterial COHb levels.

Figure 28A:
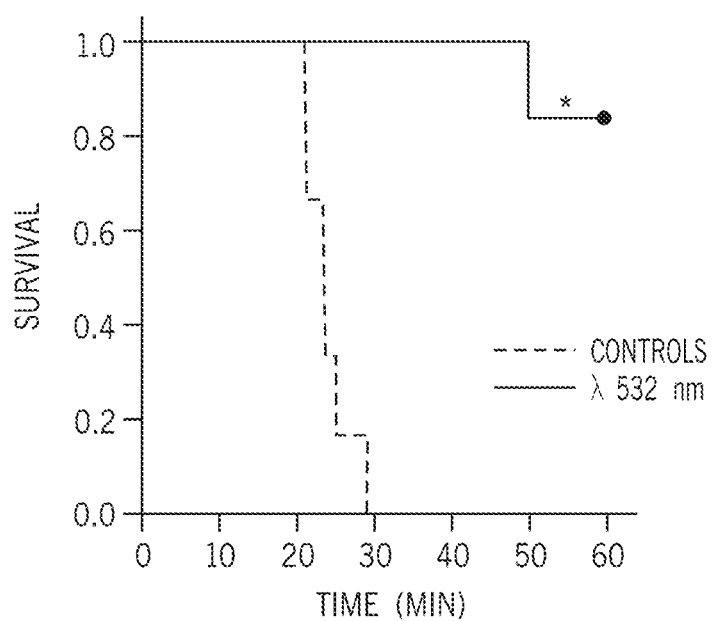
FIG. 28A shows survival rate versus time for mice with and without phototherapy at 532 nm.
Figure 28B:
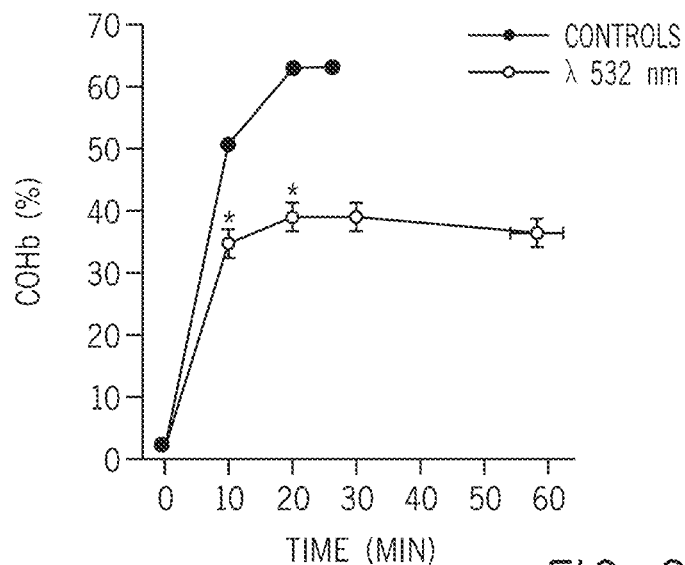
FIG. 28B shows carboxyhemoglobin percentage versus time for mince with and without phototherapy at 532 nm.
Figure 28C:
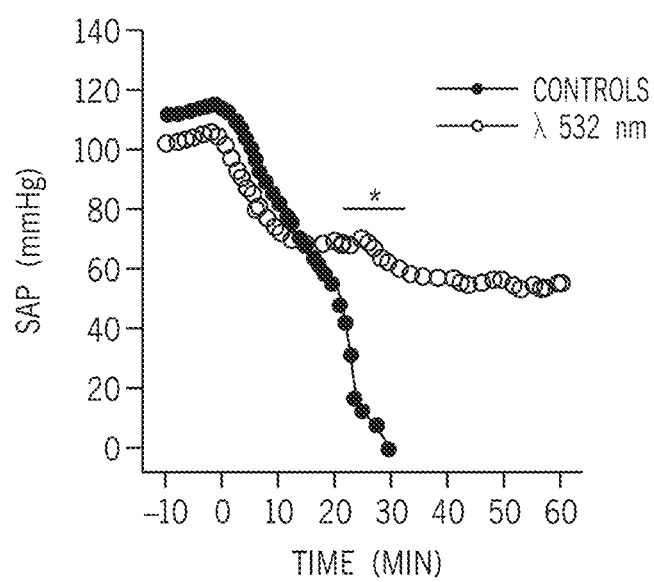
FIG. 28C shows systolic arterial pressure versus time for mice with and without phototherapy at 532 nm.
Figure 28D:
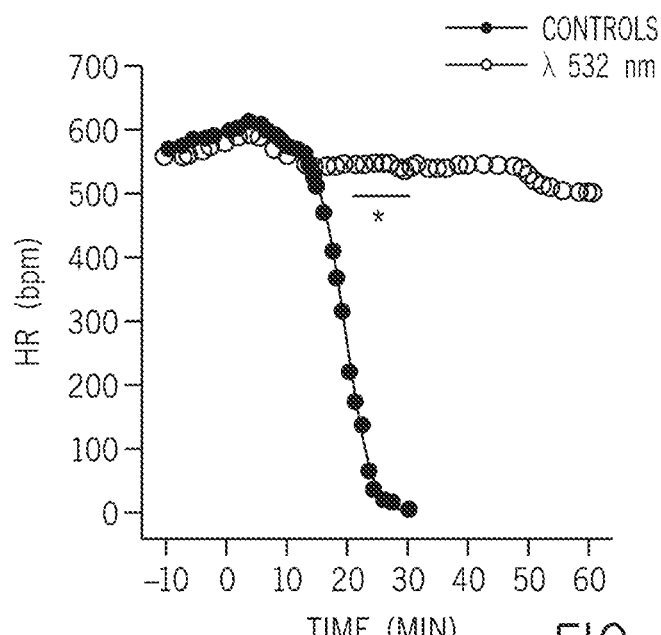
FIG. 28D shows heart rate versus time for mice with and without phototherapy at 532 nm.
Figure 28E:
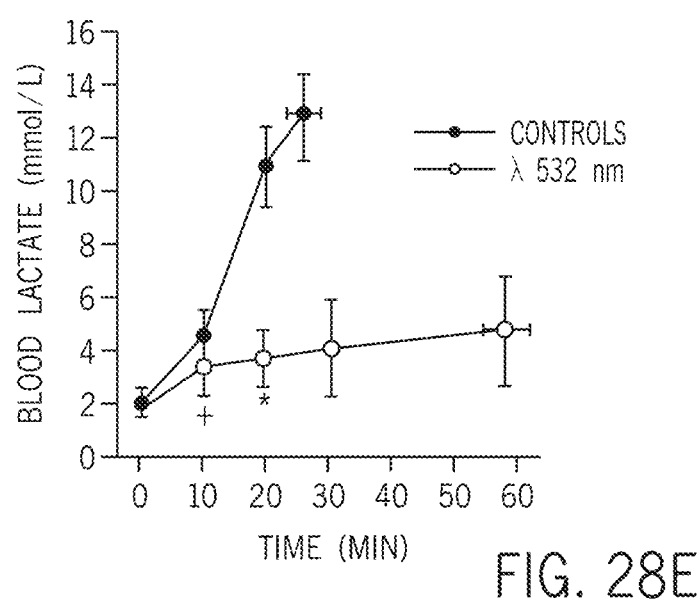
FIG. 28E shows blood lactate level versus time for mice with and without phototherapy at 532 nm.

Because phototherapy during CO poisoning decreased the amount of absorbed CO, whether phototherapy might improve the survival rate of mice breathing high levels of CO was explored. Mice breathed 2000 ppm CO in air for one hour, with or without simultaneous direct lung phototherapy at 532 nm. Without phototherapy, all of the mice died within 30 minutes of CO exposure. In contrast, 5 of 6 mice breathing CO and treated with phototherapy survived for 60 minutes, as shown in FIG. 28A. During CO poisoning, the blood COHb levels in phototherapy-treated mice were significantly less than in control mice (34.1±3.5 vs. 49.9±1.9% at 10 min and 38.5±4.0 vs. 62.0±0.9% at 20 min, respectively, p<0.001), as shown in FIG. 28B. In the first 15 minutes of CO exposure, the systolic arterial pressure decreased and the heart rate transiently increased in both groups, as shown in FIGS. 28C and 28D. Thereafter blood pressure and heart rate dramatically decreased in untreated mice while they remained constant in phototherapy-treated mice. During the study period, blood lactate levels were significantly lower in phototherapy-treated mice as compared with untreated mice ($3.4 \pm 1.0$ vs. $4.6 \pm 1.0$ mmol·L$^{-1}$ at 10 min, p=0.5 and $3.7 \pm 1.0$ vs. $11.0 \pm 1.5$ mmol·L$^{-1}$ at 20 min, p<0.001), as shown in FIG. 28E. These results show that direct lung phototherapy improves the survival rate of mice undergoing CO poisoning. The reduced degree of CO intoxication was associated with lower blood COHb and lactate levels.

Figure 29A:
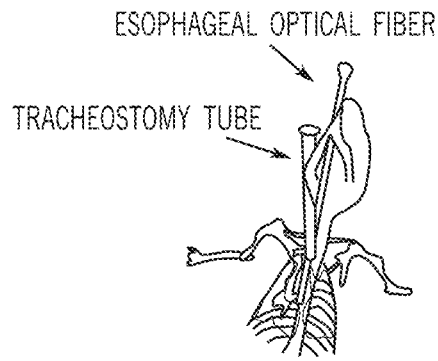
FIG. 29A shows a CT scan of a mouse with an optical fiber placed in the esophagus of the mice.

To evaluate the possibility of delivering phototherapy to murine lungs without a thoracotomy, the effect of delivering light to the lungs via an optical fiber with a diffusing tip placed via the oropharynx into the esophagus was explored. To optimize the position of the esophageal optical fiber in relation to the lungs, a CT scan of a living, anesthetized and mechanically ventilated 25 g mouse was captured, as shown in FIG. 29A. The optimal location of the fiber to irradiate the lower portion of the lungs was reached when the end of the fiber was 3.9 cm from the mandibular incisors.

Figure 29B:
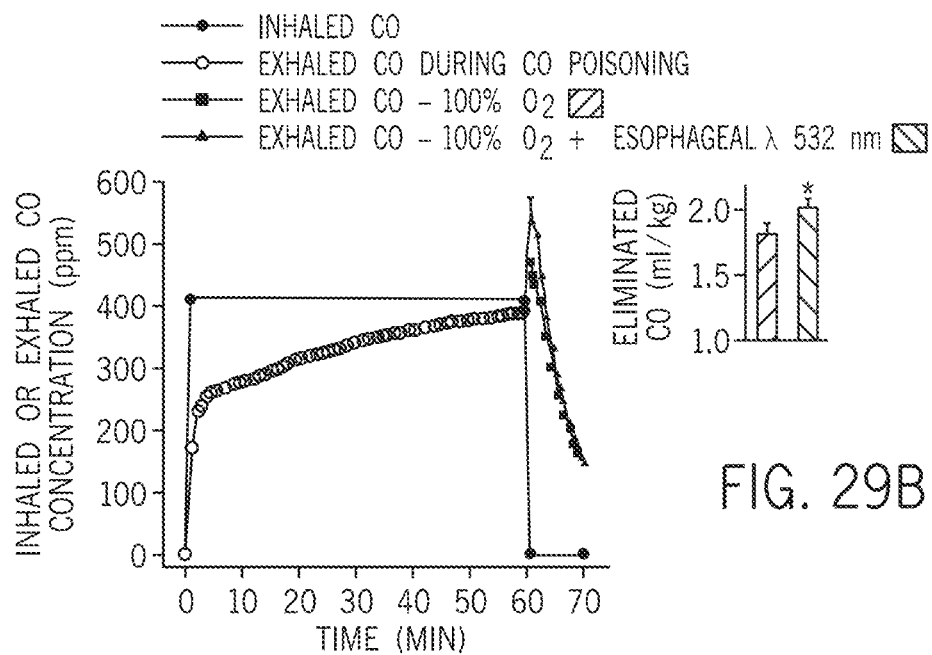
FIG. 29B shows inhaled or exhaled carbon monoxide concentration versus time for mice breathing 100% oxygen with and without esophageal phototherapy.
Figure 29C:
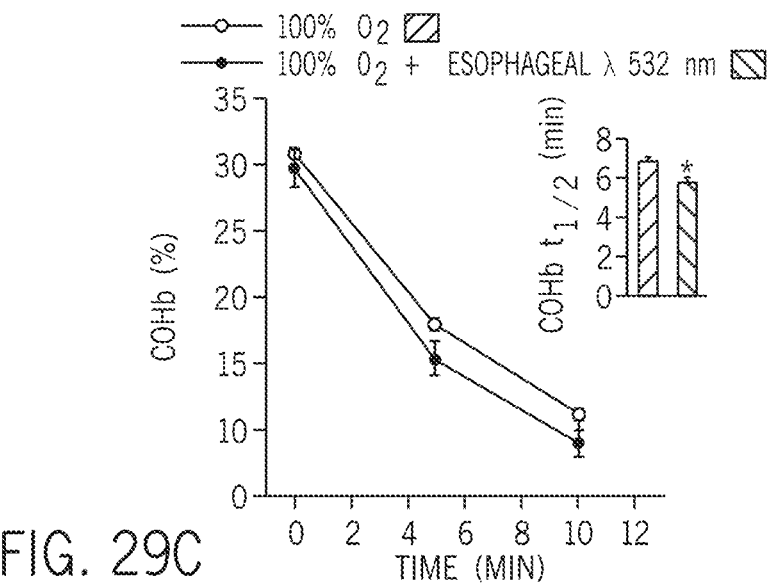
FIG. 29C shows carboxyhemoglobin percentage versus time for mice breathing 100% oxygen with and without esophageal phototherapy.

After breathing 400 ppm CO for one hour, mice were treated by ventilation with 100% $O_2$ alone or combined with trans-esophageal phototherapy of the lung. The quantity of CO eliminated during the first 5 minutes of treatment was significantly greater in mice treated with esophageal phototherapy (AUC: $2246 \pm 85$ vs. $2030 \pm 83$ respectively, p=0.001), as shown in FIG. 29B, and COHb-$t_{1/2}$ was significantly shorter with phototherapy than in mice breathing 100% $O_2$ alone ($5.7 \pm 0.3$ vs. $6.8 \pm 0.3$ min, p<0.001), as shown in FIG. 29C. These results demonstrate that esophageal phototherapy increased the rate of CO elimination when compared to 100% $O_2$ breathing alone.

Rat Studies

To further test the efficacy of the phototherapy systems and methods described herein, pulmonary phototherapy was tested in rats, an animal weighing approximately 18 times more than mice. All animal experiments were approved by the Subcommittee on Research Animal Care of the Massachusetts General Hospital, Boston, MA. 49 male Sprague Dawley rats (Charles River Laboratories, Wilmington, MA, USA) weighing $454 \pm 69$ g (mean±SD) were tested. Rats were anesthetized with intraperitoneal (i.p.) ketamine (100 mg·kg$^{-1}$) and fentanyl (50 mcg·kg$^{-1}$). Following a tracheostomy, rocuronium (1 mg·kg$^{-1}$) was injected i.p. to induce muscle relaxation and rats were mechanically ventilated (Inspira; Harvard Apparatus, Holliston, MA, USA). Volume-controlled ventilation was provided at a respiratory rate of 40 breaths·min$^{-1}$, a tidal volume of 10 ml·kg$^{-1}$, positive end expiratory pressure (PEEP) of 2 cm $H_2O$ and inspired oxygen fraction (FIO$_2$) of 0.21. Catheters were placed in the carotid artery and jugular vein. Arterial blood pressure, heart rate, body temperature and peak airway pressure were continuously monitored. Continuous i.v. anesthesia and muscle relaxation were provided with fentanyl (1.2-2.4 mcg·kg$^{-1}$·h$^{-1}$), ketamine (10-20 mg·kg$^{-1}$·h$^{-1}$) and rocuronium (2-4 mg·kg$^{-1}$·h$^{-1}$). Ringer's Lactate was infused at a rate of 8-12 ml·kg$^{-1}$·h$^{-1}$.

Figure 30A:
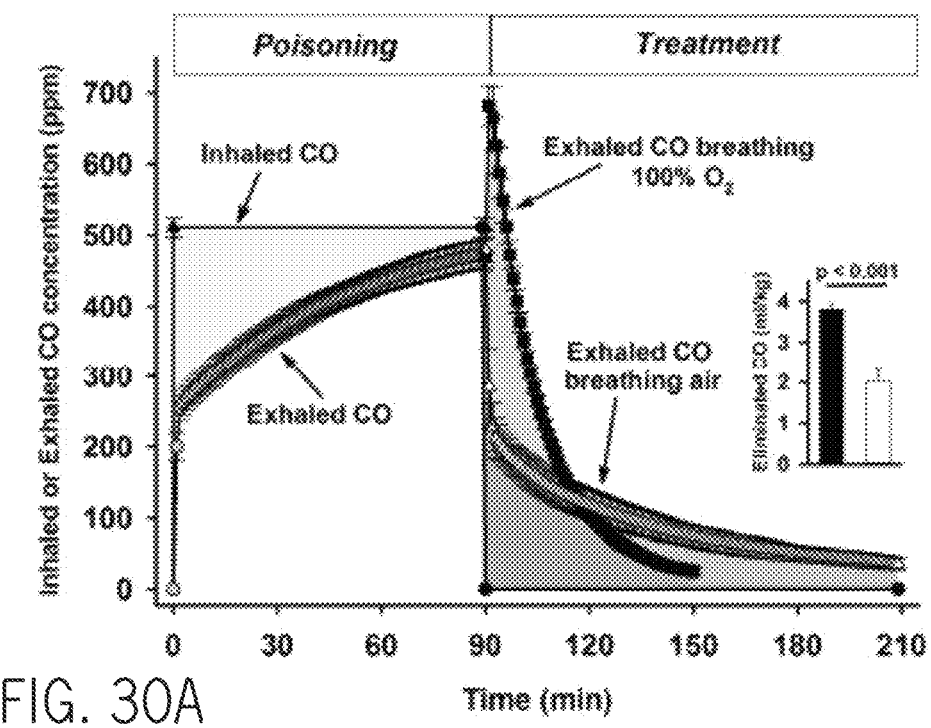
FIG. 30A shows inhaled or exhaled carbon monoxide concentration versus time during phototherapy of rats breathing either air or 100% oxygen poisoned with 500 ppm CO for 90 minutes.
Figure 30B:
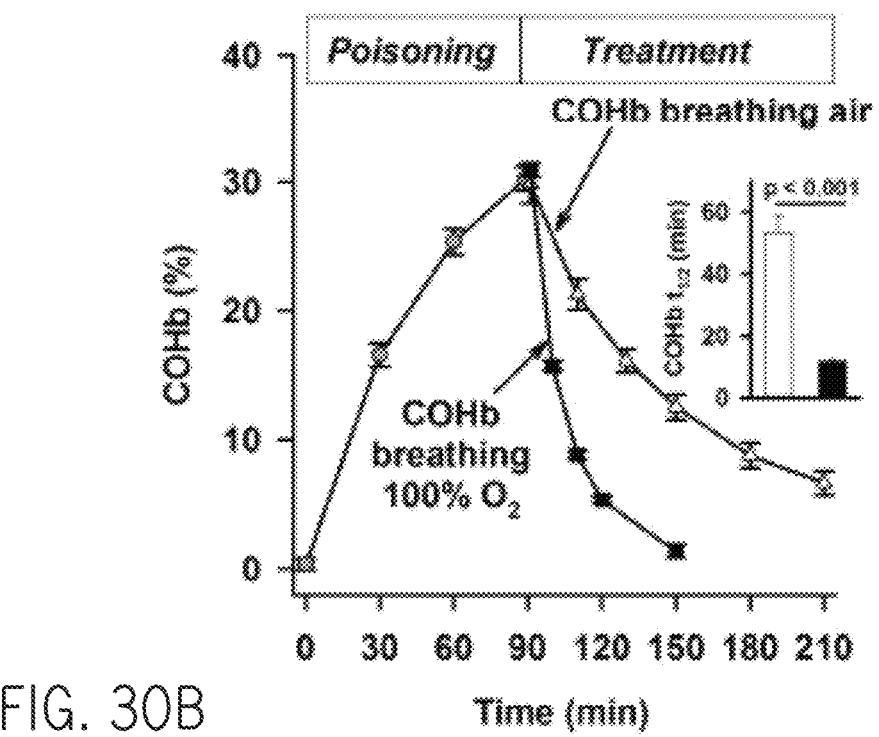
FIG. 30B shows carboxyhemoglobin percentage as a function of time during phototherapy of rats breathing either air or 100% oxygen after poisoning with 500 ppm CO for 90 minutes.

To test whether direct phototherapy could increase the rate of CO elimination in an animal that is 18 times heavier than a mouse, a model of CO poisoning in rats was developed. Anesthetized and mechanically ventilated rats were poisoned for 90 minutes breathing 500 ppm CO in air, and then treated with either air or 100% oxygen. As observed during the poisoning period in mice (FIGS. 23A and 23B), the exhaled CO concentration slowly increased, indicating that a large amount of CO was absorbed by the rat at the beginning of poisoning, as shown in FIG. 30A. Over time, smaller amounts CO were absorbed as the circulating hemoglobin became progressively saturated with CO. After the poisoning period, rats were treated by breathing either 100% oxygen or room air at a constant minute ventilation. During the first 30 minutes of treatment breathing 100% oxygen, the exhaled CO concentration was significantly greater than that of rats breathing air, and the calculated quantity of CO eliminated during this time was significantly greater ($3.8 \pm 0.1$ vs. $2.0 \pm 0.3$ ml·kg–1, p<0.001). In parallel, blood COHb decreased faster, and COHb-$t_{1/2}$ was shorter when rats breathed 100% oxygen (100% oxygen vs. room air: $12.0 \pm 0.5$ vs. $53.5 \pm 5.1$ min, p<0.001), as shown in FIG. 30B. These results show that the rat model of CO poisoning is suitable for studying the effects of various treatments on the rate of CO elimination.

To directly illuminate the lungs, anesthetized rats underwent a median thoracotomy. Light at 532 nm wavelength was generated by an Aura KTP laser (American Medical Systems, Minnetonka, Minnesota, USA) and delivered to both lungs via an optical fiber. The tip of the fiber was placed at 10 cm distance from the lung's surface, so that the area of the light beam was sufficiently wide to illuminate the anterior surface of each lung. The power of the laser was set to illuminate the lungs with an irradiance of 54 mW·cm$^{-2}$.

Figure 31A:
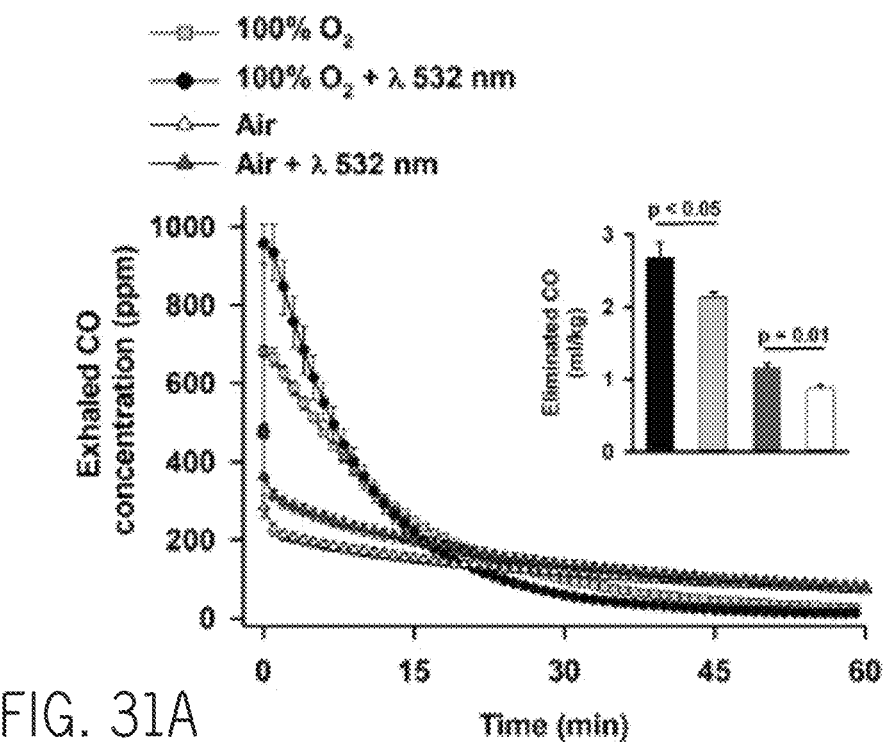
FIG. 31A shows exhaled carbon monoxide concentration as a function of time with and without phototherapy at 532 nm of rats breathing either air or 100% oxygen after poisoning with 500 ppm CO for 90 minutes.
Figure 31B:
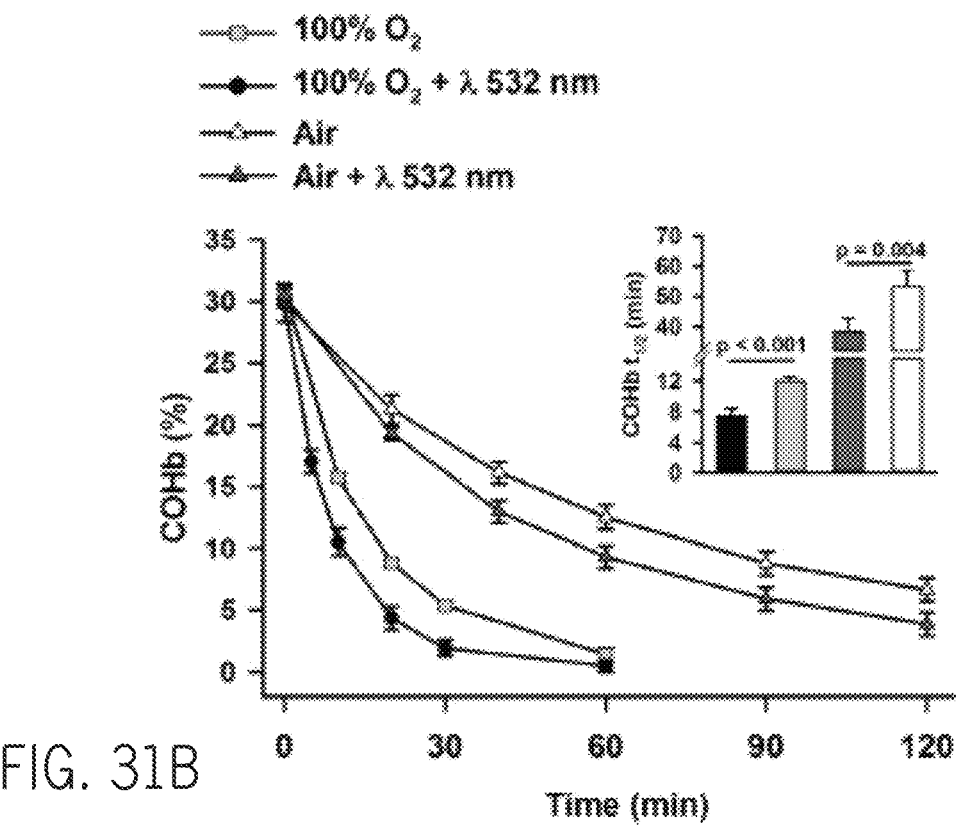
FIG. 31B shows carboxyhemoglobin percentage as a function of time with and without phototherapy at 532 nm of rats breathing either air or 100% oxygen after poisoning with 500 ppm CO for 90 minutes.

To test whether phototherapy increases the CO elimination rate, rats were poisoned by breathing CO at 500 ppm for 90 minutes in air and then treated by breathing either air or 100% oxygen with or without adding direct lung phototherapy. As shown in FIG. 31A, when animals were treated with either 100% oxygen or room air, the addition of pulmonary phototherapy significantly increased the rate of CO elimination, as demonstrated by a greater amount of exhaled CO measured during the first 10 minutes of treatment (100% oxygen vs. 100% oxygen plus phototherapy: $2.2 \pm 0.1$ vs. $2.7 \pm 0.4$ ml·kg–1, p<0.5; air vs. air plus phototherapy: $0.9 \pm 0.1$ vs. $1.2 \pm 0.1$ ml·kg–1, p=0.1). Concomitantly, as shown in FIG. 31B, there was a more rapid reduction of blood COHb levels (COHb-$t_{1/2}$: 100% oxygen vs. 100% oxygen plus phototherapy: $12.0 \pm 0.5$ vs. $7.4 \pm 1.0$ min, p<0.001; air vs. air plus phototherapy: $53.5 \pm 5.1$ vs. $38.4 \pm 4.6$ min, p=0.004). These results demonstrate that direct pulmonary phototherapy increases the rate of CO elimination in rats breathing either air or 100% oxygen.

Figure 32B:
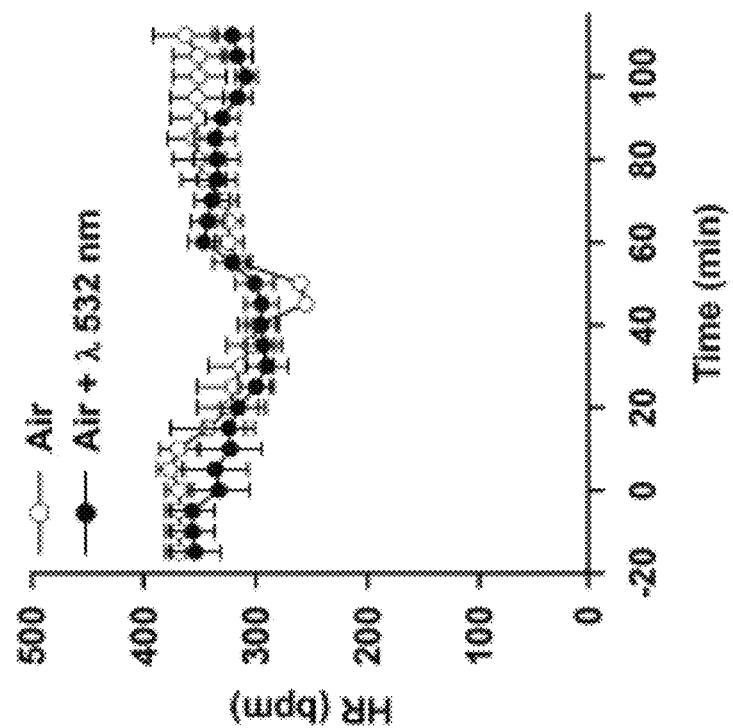
FIG. 32B shows heart rate as a function of time with and without phototherapy at 532 nm of rats breathing air after poisoning with 500 ppm CO for 90 minutes.
Figure 32A:
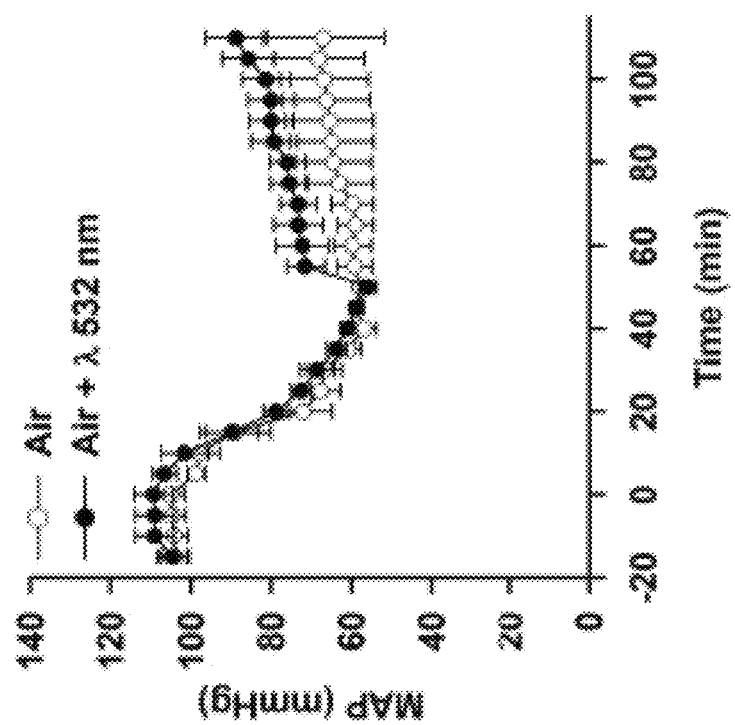
FIG. 32A shows mean arterial pressure as a function of time with and without phototherapy at 532 nm of rats breathing air after poisoning with 500 ppm CO for 90 minutes.
Figure 32D:
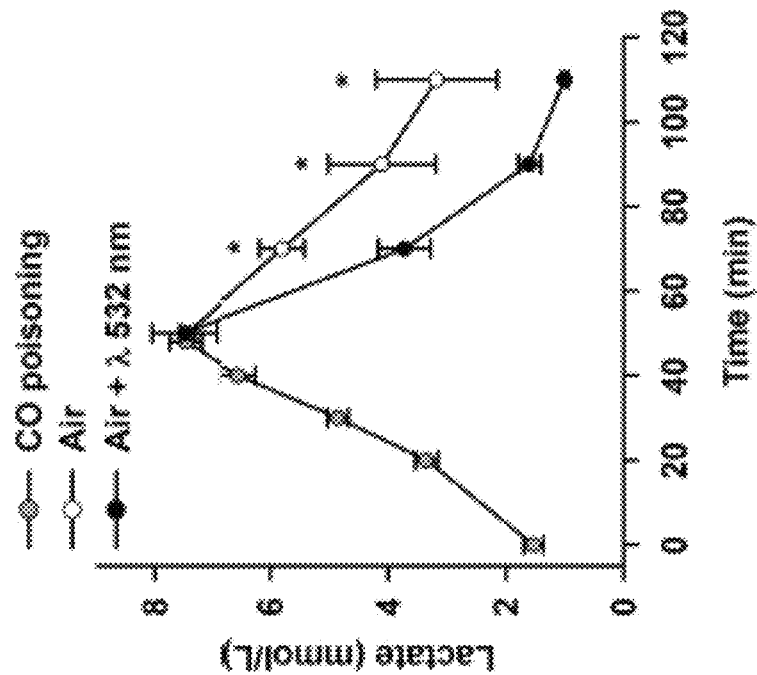
FIG. 32D shows lactate levels as a function of time with and without phototherapy at 532 nm of rats breathing air after poisoning with 500 ppm CO for 90 minutes.
Figure 32C:
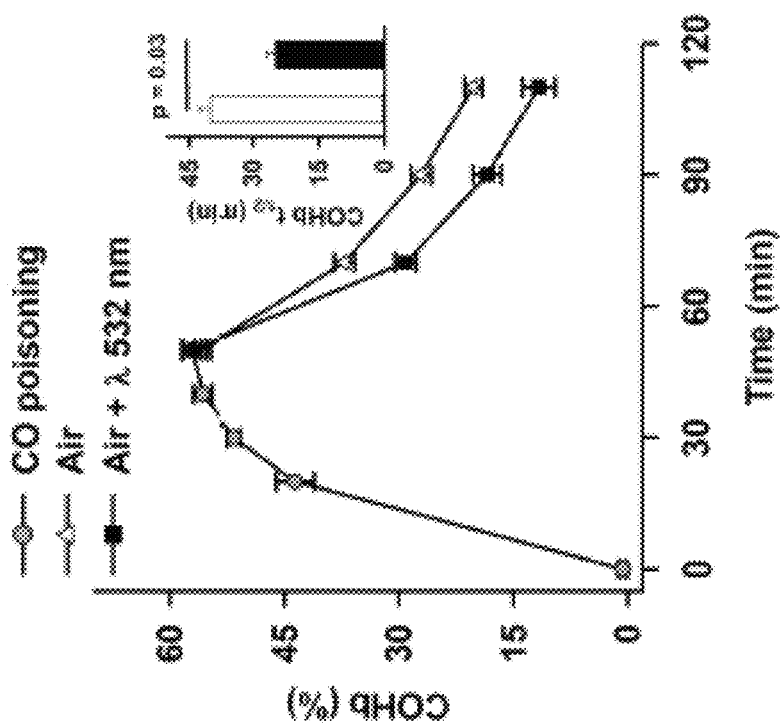
FIG. 32C shows carboxyhemoglobin percentage as a function of time with and without phototherapy at 532 nm of rats breathing air after poisoning with 500 ppm CO for 90 minutes.

To study whether the more rapid reduction of COHb levels observed with phototherapy could have a salutary effect on oxygen delivery and metabolism after severe CO poisoning, rats were exposed to breathing 2000 ppm CO in air until their blood lactate levels reached a concentration of 7 mmol/L or higher. All animals reached the target lactate concentration within 50 minutes of breathing CO; animals were then treated by breathing air with or without phototherapy. As shown in FIGS. 32A and 32B, during the poisoning period the mean arterial pressure and the heart rate decreased from $107 \pm 3$ to $56 \pm 1$ mmHg and from $350 \pm 15$ to $293 \pm 12$ beats/min respectively (mean±SEM). Mean arterial pressure and heart rate during treatment were not different in phototherapy-treated rats as compared with rats breathing air alone. Importantly, the COHb level decreased faster during treatment with phototherapy. The blood lactate concentration was also lower after 20, 40 and 60 minutes of treatment with phototherapy and room air compared to room air alone (20 minutes: $3.7 \pm 0.5$ vs. $5.8 \pm 0.4$ mmol/L, p=0.1; 40 minutes: $1.6 \pm 0.2$ vs. $4.1 \pm 0.9$ mmol/L, p=0.009; 60 minutes: $1.0 \pm 0.1$ vs. $3.2 \pm 1.0$ mmol/L, p=0.2), as shown in FIGS.

32C and 32D. These results show that CO-poisoned rats breathing air and treated with pulmonary phototherapy have improved lactate clearance.

Figure 33A:
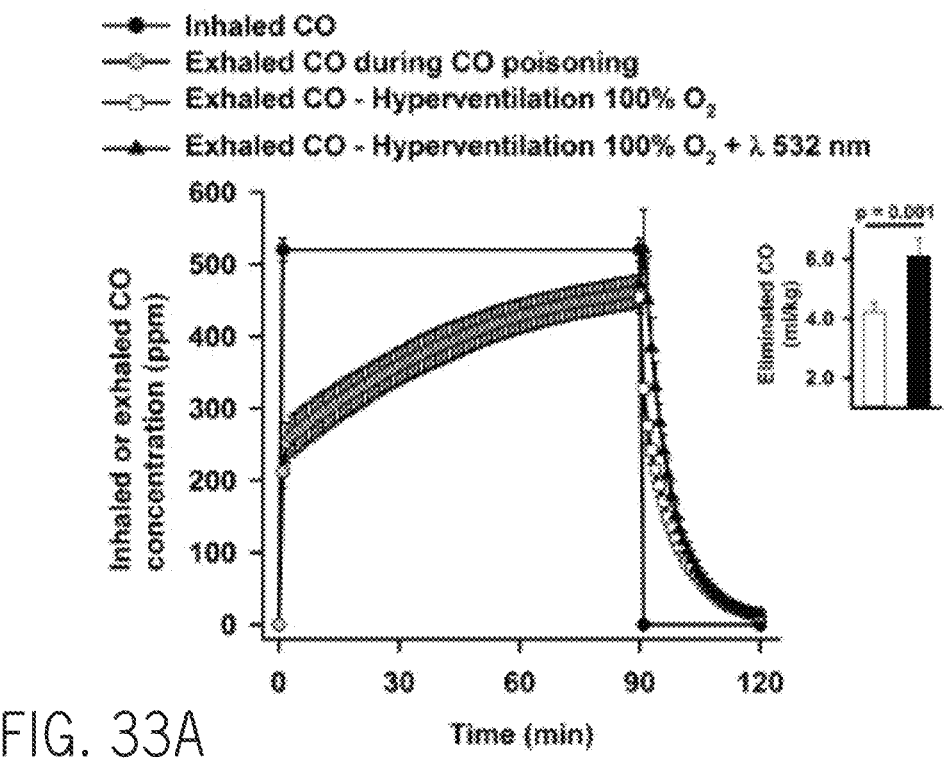
FIG. 33A shows inhaled or exhaled carbon monoxide concentration as a function of time with or without hyperventilation and phototherapy at 532 nm of rats breathing 100% oxygen after poisoning with 500 ppm CO for 90 minutes.
Figure 33B:
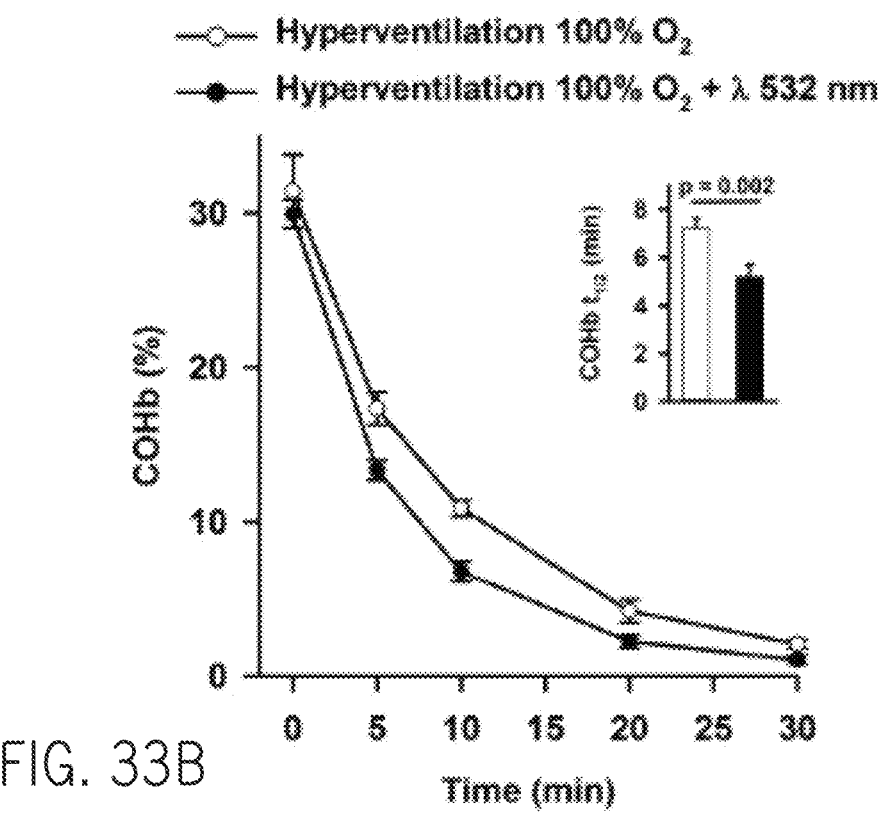
FIG. 33B shows carboxyhemoglobin percentage as a function of time with or without hyperventilation and phototherapy at 532 nm of rats breathing 100% oxygen after poisoning with 500 ppm CO for 90 minutes.

To study whether the combination of isocapnic hyperventilation and pulmonary phototherapy would augment the rate of CO elimination, anesthetized and mechanically ventilated rats were poisoned by breathing 500 ppm CO in air for 90 minutes and then treated with isocapnic hyperventilation with or without direct lung phototherapy at 54 mW·cm−2. Despite a slightly lower inspired oxygen concentration (approximately 95% vs. 100%) due to the addition of 5% CO2 to maintain a constant arterial PaCO2 and avoid hypocapnia, animals treated with isocapnic hyperventilation had a more rapid decrease of blood COHb levels compared to animals treated with 100% oxygen with a normal minute ventilation rate (COHb-$t_{1/2}$: 7.1±0.4 vs. 12.0±0.5 min, p<0.001). The combination of direct pulmonary phototherapy and isocapnic hyperventilation increased the rate of CO elimination as compared with isocapnic hyperventilation alone, as demonstrated by a larger amount of CO eliminated during the first ten minutes of treatment (isocapnic hyperventilation plus phototherapy vs. isocapnic hyperventilation alone: 6.1±0.6 vs. 4.2±0.3 ml·kg−1, p=0.001), as shown in FIG. 33A. Also, a decreased COHb-$t_{1/2}$ (5.2±0.5 vs. 7.1±0.4 min, p=0.002) was observed, as shown in FIG. 33B. These results show that increased minute ventilation increases the rate of CO elimination in rats. Moreover, combining pulmonary phototherapy and isocapnic hyperventilation with 95% oxygen can further increase the rate of CO elimination.

Intrapleural phototherapy was tested using two optical fibers with 3.5 cm long diffusing tips emitting light in all directions were placed in the right and left pleural spaces of rats. In anesthetized, mechanically ventilated supine rats, 1.5 cm long incisions were made in the abdominal wall in the right and left hypochondriac regions. After exposing the abdominal cavity and the lower surface of the diaphragm, two 2 mm incisions were made in the diaphragm and one optical fiber was placed in both the right and left pleural spaces. To irradiate each lung with sufficient power, the right fiber was connected to the Aura KTP laser and the left fiber was connected to a frequency-doubled Nd:YAG laser (IRIDEX Corp., Mountain View, CA), both lasers generating light at 532 nm. The power of the light emitted by the diffusing optical fibers was 570 (right pleural space) and 450 (left pleural space) mW.

To treat CO poisoning with direct lung irradiation, the intrapleural approach to light delivery to the lungs was employed. After 90 minutes of poisoning with 500 ppm CO, rats were treated with 100% oxygen with or without intrapleural phototherapy. Compared with rats treated with 100% oxygen alone, intrapleural phototherapy combined with 100% oxygen was associated with a greater quantity of CO elimination during the first ten minutes of treatment (2.4±0.2 vs. 2.1±0.1 ml·kg−1, p=0.009), as shown in FIG. 34A, and a shorter COHb-$t_{1/2}$ (9.8±0.5 vs. 11.7±0.3 min, p<0.001), as shown in FIG. 34B. These results demonstrate that intrapleural phototherapy can increase the rate of CO elimination in a CO poisoned rat breathing 100% oxygen.

Figure 35:
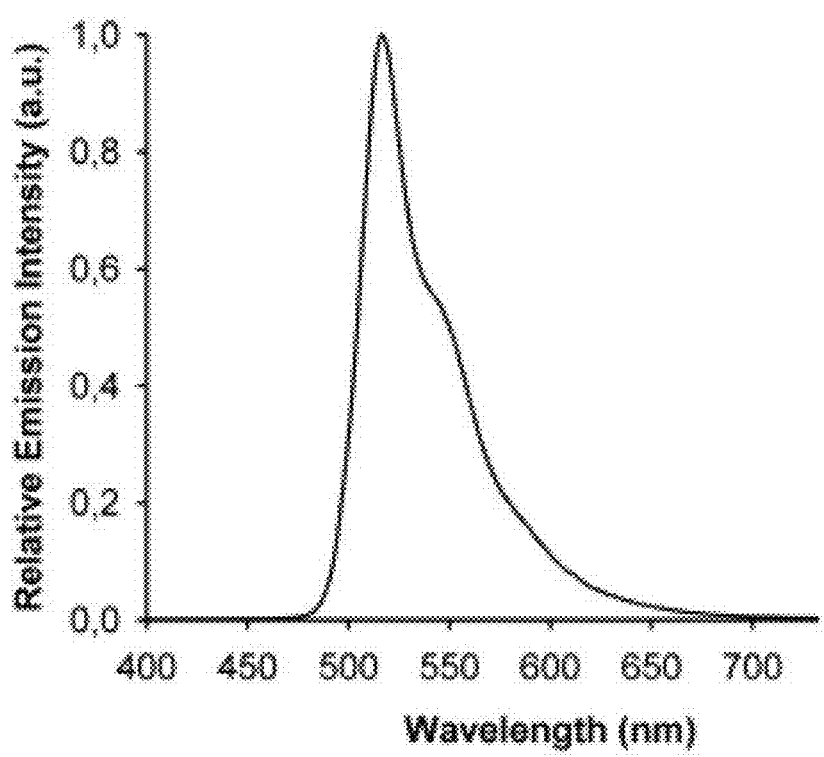
FIG. 35 shows a light spectrum produced by a chemiluminescence reaction used for chemiluminescence phototherapy.

Whether light generated by chemiluminescence would dissociate CO in vivo and increase the rate of CO elimination was tested. The light spectrum generated by the chemiluminescence reaction was measured with a spectrophotometer, showing a peak wavelength of 517 nm and a central wavelength of 532 nm (bandwidth (90%)=110 nm), as shown in FIG. 35. In anesthetized rats at thoracotomy, a custom-fabricated clear polyethylene sack was placed around each lung. Each sack had a small catheter allowing the injection of chemiluminescent fluid into the sack. After 90 minutes of CO poisoning, the luminescent fluid was injected into the polyethylene bags while the animal breathed 100% oxygen. In control animals, the polyethylene bags were filled with an equal volume of saline.

Figure 36B:
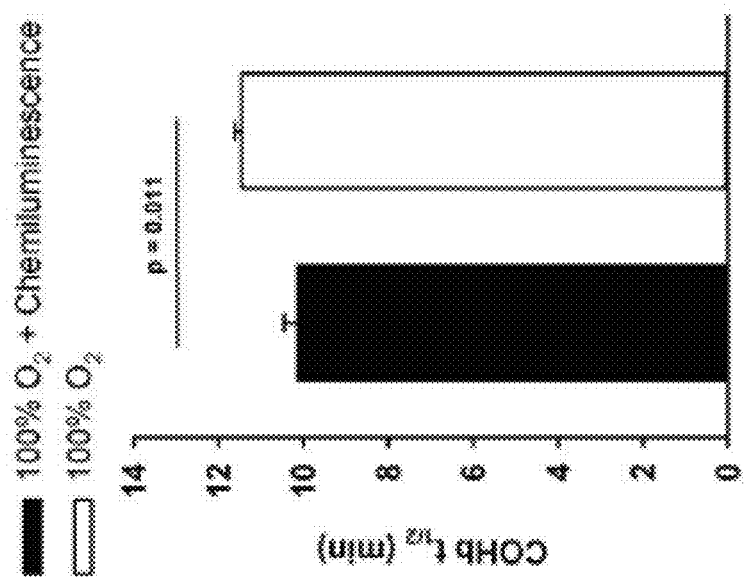
FIG. 36B shows carboxyhemoglobin half-life with and without chemiluminescence phototherapy at 532 nm of rats breathing 100% oxygen after poisoning with 500 ppm CO for 90 minutes.
Figure 36A:
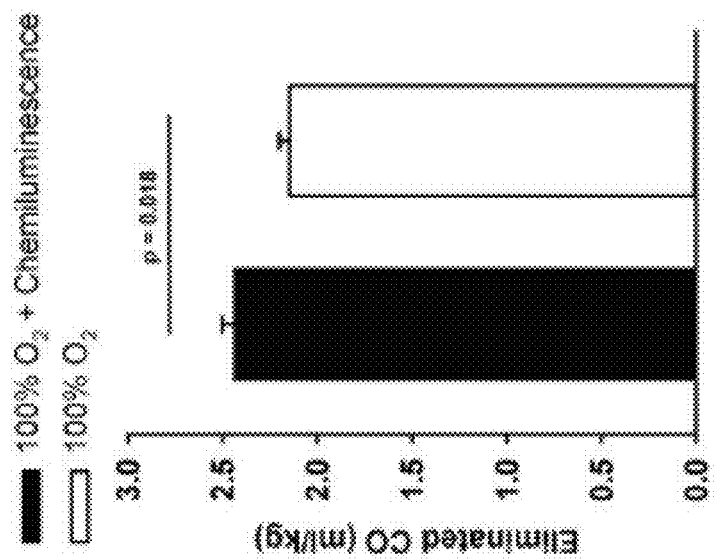
FIG. 36A shows eliminated carbon monoxide with and without chemiluminescence phototherapy at 532 nm of rats breathing 100% oxygen after poisoning with 500 ppm CO for 90 minutes.

To test the efficacy of the chemiluminescence approach, CO elimination rate in CO-poisoned rats was measured. After 90 minutes of CO poisoning by breathing 500 ppm CO in air, rats were treated with 100% oxygen with or without light emitted by a chemiluminescent fluid injected into the two clear sacks. The amount of CO exhaled during the first ten minutes of treatment was greater in rats treated with 100% oxygen and chemiluminescence-generated phototherapy as compared to rats breathing 100% oxygen alone (2.4±0.1 vs. 2.1±0.1 ml·kg−1, p=0.018), as shown in FIG. 36A, and the COHb-$t_{1/2}$ was significantly shorter (10.1±0.6 vs. 11.5±0.3 min, p=0.11), as shown in FIG. 36B. These results show that providing green light generated by a chemiluminescent reaction in both pleural spaces can increase the rate of CO elimination, suggesting that protected chemiluminescent light sources might be used to irradiate the lungs.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A phototherapy system for treating or controlling an amount of carbon monoxide poisoning in a patient, comprising:
    a light source in communication with an aerosolizing element; and
    a tube configured to provide communication between the light source and an airway, the airway configured to provide communication to at least one of a nose and a mouth of the patient,
    wherein the aerosolizing element is configured to aerosolize the light source to deliver the light source to the patient by ventilation of gas through the airway, wherein the light source is a plurality of phosphorescent particles.

2. The phototherapy system of claim 1, wherein the light source is configured to emit light at a wavelength between approximately 390 nanometers and 750 nanometers.

3. The phototherapy system of claim 1, wherein the aerosolizing element is configured to aerosolize a specific number of phosphorescent particles to achieve a predetermined a particle load to be inhaled by the patient.

4. The phototherapy system of claim 1, wherein the phosphorescent particles define varying diameters such that, when inhaled, the phosphorescent particles are located throughout a trachea and a bronchial tract of the patient.

5. The phototherapy system of claim 1, wherein the phosphorescent particles are chemically inert and non-toxic to humans.

6. The phototherapy system of claim 1, further comprising an excitation source configured to activate the phosphorescent particles.

7. The phototherapy system of claim 6, wherein the excitation source is at least one of a laser, a lamp, and one or more light-emitting-diodes.

8. The phototherapy system of claim 6, further comprising a controller in communication with the excitation source and the aerosolizing element.

9. The phototherapy system of claim 1, further comprising a gas source in communication with the light source.

10. The phototherapy system of claim 9, wherein the gas source is a pressurized supply or air or oxygen.

11. The photo therapy system of claim 1, wherein the airway comprises at least one of a mask, a respirator, nasal prongs, an endotracheal tube, and a tracheostomy tube.

* * * * *

UNITED STATES PATENT AND TRADEMARK OFFICE
CERTIFICATE OF CORRECTION

PATENT NO. : 11,826,580 B2
APPLICATION NO. : 17/202878
DATED : November 28, 2023
INVENTOR(S) : Warren M. Zapol et al.

Page 1 of 1

It is certified that error appears in the above-identified patent and that said Letters Patent is hereby corrected as shown below:

In the Specification

Column 8, Line 38, "Dc" should be --$D_t$--.

Column 19, Line 11, "02" should be --$O_2$--.

Column 20, Line 49, "16.8 1.1" should be --$16.8 \pm 1.1$--.

Signed and Sealed this
Twenty-seventh Day of February, 2024

Katherine Kelly Vidal
*Director of the United States Patent and Trademark Office*